(12) United States Patent
Shioi et al.

(10) Patent No.: US 12,099,062 B2
(45) Date of Patent: Sep. 24, 2024

(54) PATHOGEN DETECTION SYSTEM AND PATHOGEN DETECTION METHOD

(71) Applicant: Panasonic Intellectual Property Management Co., Ltd., Osaka (JP)

(72) Inventors: Masahiko Shioi, Osaka (JP); Osamu Akasaka, Hyogo (JP); Noriaki Fukumoto, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 939 days.

(21) Appl. No.: 16/840,493

(22) Filed: Apr. 6, 2020

(65) Prior Publication Data

US 2020/0232992 A1     Jul. 23, 2020

Related U.S. Application Data

(63) Continuation of application No. PCT/JP2018/043674, filed on Nov. 28, 2018.

(30) Foreign Application Priority Data

Dec. 25, 2017  (JP) ................. 2017-248435

(51) Int. Cl.
| | | |
|---|---|---|
| G01N 1/02 | (2006.01) | |
| G01N 33/00 | (2006.01) | |
| G01N 33/50 | (2006.01) | |
| G01N 33/543 | (2006.01) | |
| G01N 33/569 | (2006.01) | |
| G01N 33/58 | (2006.01) | |
| G01N 1/22 | (2006.01) | |

(52) U.S. Cl.
CPC ....... *G01N 33/582* (2013.01); *G01N 33/0075* (2013.01); *G01N 33/5091* (2013.01); *G01N 33/54373* (2013.01); *G01N 33/56983* (2013.01); *G01N 1/2273* (2013.01)

(58) Field of Classification Search
CPC .......... G01N 33/00; G01N 33/0004; G01N 33/0009; G01N 33/073; G01N 33/0075; G01N 33/54373; G01N 33/56988; G01N 1/02; G01N 1/22; G01N 1/2273; G01N 1/26; G01N 2001/021; G01N 33/497
See application file for complete search history.

(56) References Cited

U.S. PATENT DOCUMENTS

| | | | |
|---|---|---|---|
| 2004/0043443 A1 | 3/2004 | Lejeune | |
| 2014/0191875 A1* | 7/2014 | Wedig | G08B 21/22 340/628 |
| 2016/0041074 A1* | 2/2016 | Pliskin | G01N 15/0625 422/3 |
| 2016/0379814 A1 | 12/2016 | Yamada et al. | |

FOREIGN PATENT DOCUMENTS

| | | | |
|---|---|---|---|
| JP | 2005-520169 | 7/2005 | |
| JP | 2005-275708 | 10/2005 | |
| JP | 2012-052866 | 3/2012 | |
| JP | 2015-206670 A * | 11/2015 | ............... G01N 1/02 |
| WO | 2015/136695 | 9/2015 | |

OTHER PUBLICATIONS

Jelicic et al., "Context-Adaptive Multimodal Wireless Sensor Network for Energy-Efficient Gas Monitoring", Jan. 2013, IEEE Sensors Journal, vol. 13, No. 1, p. 328-338 (Year: 2013).*
International Search Report of PCT application No. PCT/JP2018/043674 dated Mar. 5, 2019.

* cited by examiner

*Primary Examiner* — Ann Montgomery
(74) *Attorney, Agent, or Firm* — Wenderoth, Lind & Ponack, L.L.P.

(57) ABSTRACT

A pathogen detection system includes pathogen detectors disposed in different locations, and a controller. The pathogen detectors include a first pathogen detector and a second pathogen detector. The first pathogen detector transmits a first detection result obtained as a result of pathogen detection to the controller, and the second pathogen detector transmits a second detection result obtained as a result of pathogen detection to the controller. In a case where the first detection result satisfies a predetermined condition, the controller causes the second pathogen detector to change a mode related to the pathogen detection from a first mode to a second mode.

8 Claims, 17 Drawing Sheets

FIG. 6

| PATHOGEN DETECTOR ID | PATHOGEN CONCENTRATION | DETECTION TIME |
|---|---|---|
| 10a | 100 | 2017/8/3 13:30 |
| 10b | 0 | 2017/8/3 13:30 |
| 10c | 20 | 2017/8/3 13:30 |
| ... | ... | ... |
| 10p | 5 | 2017/8/3 13:30 |

FIG. 7

START
↓
S11 COLLECT MICROPARTICLES
↓
S12 SEPARATE MICROPARTICLES FROM AIR
↓
S13 EXTRACT PATHOGEN
↓
S14 INTRODUCE SAMPLE FLUID
↓
S15 IRRADIATE WITH EXCITATION LIGHT
↓
END

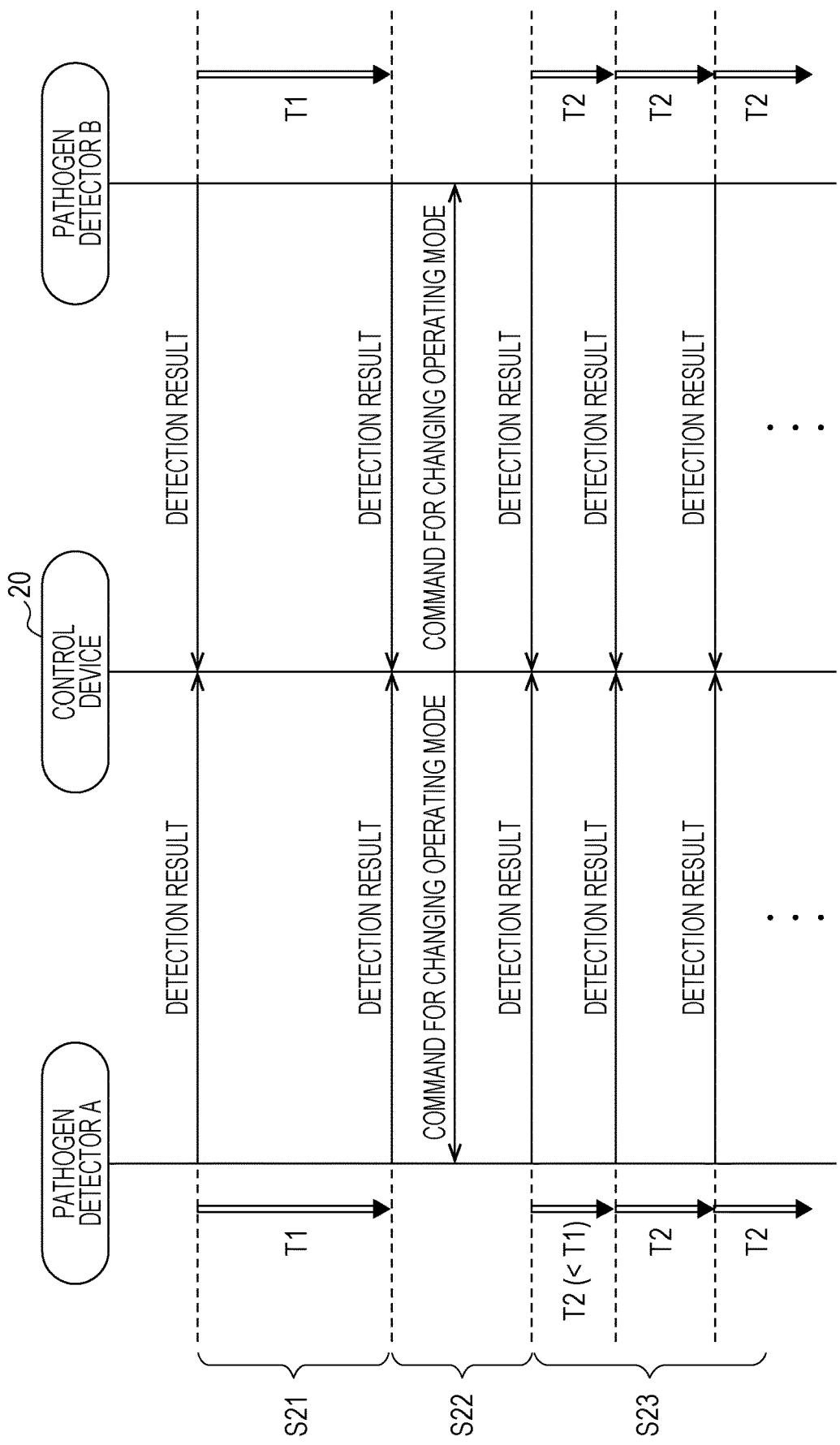

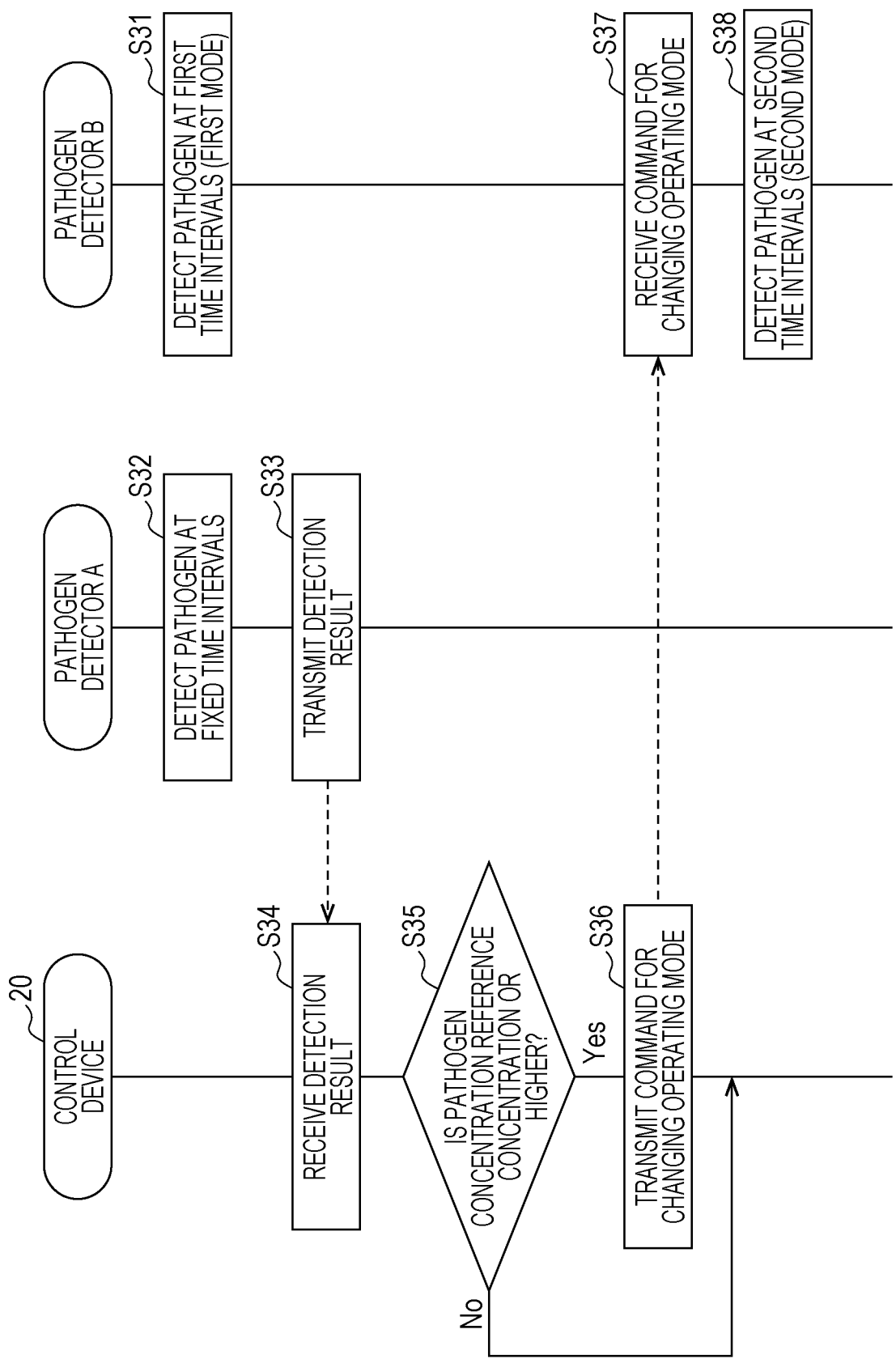

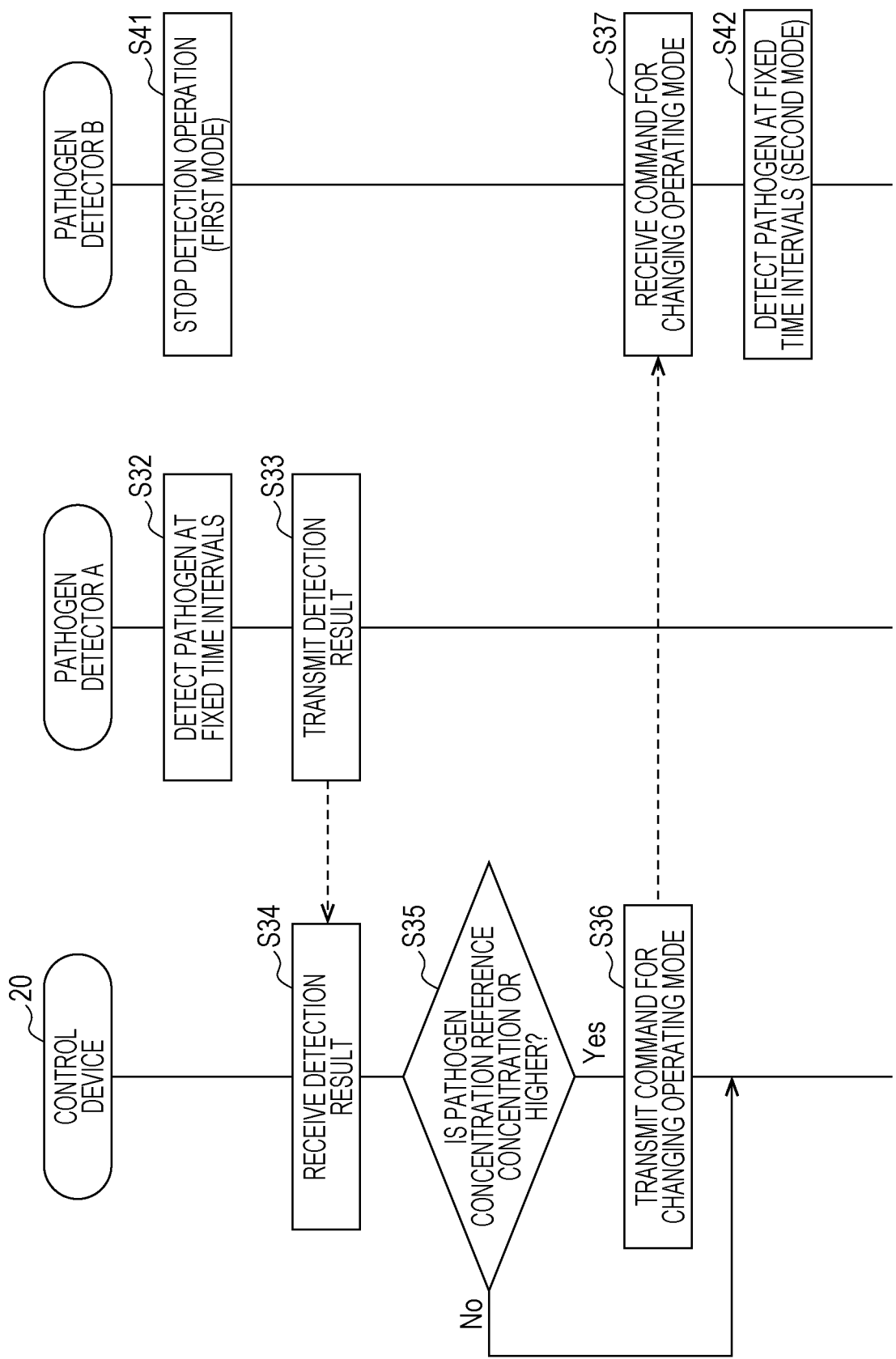

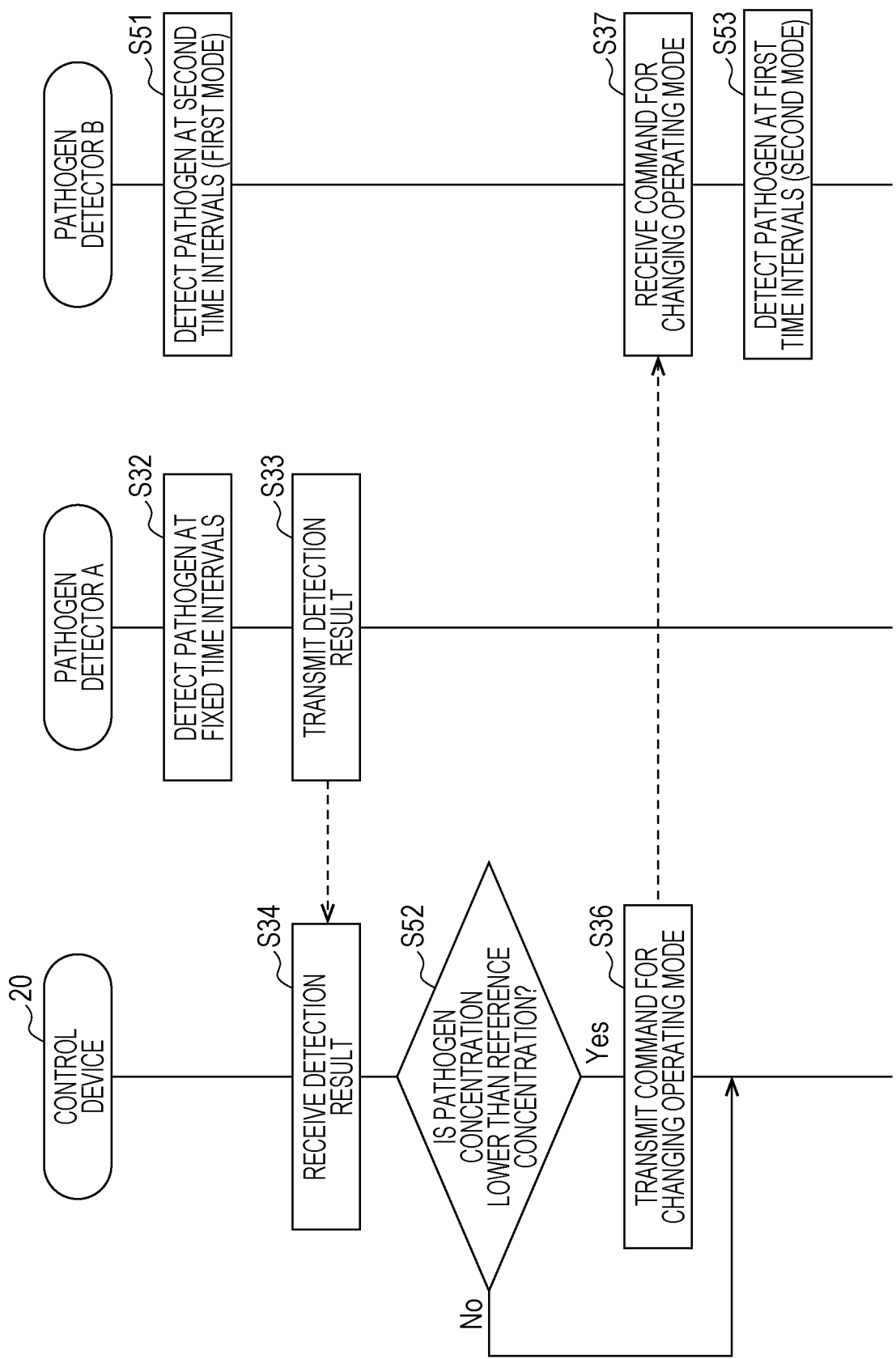

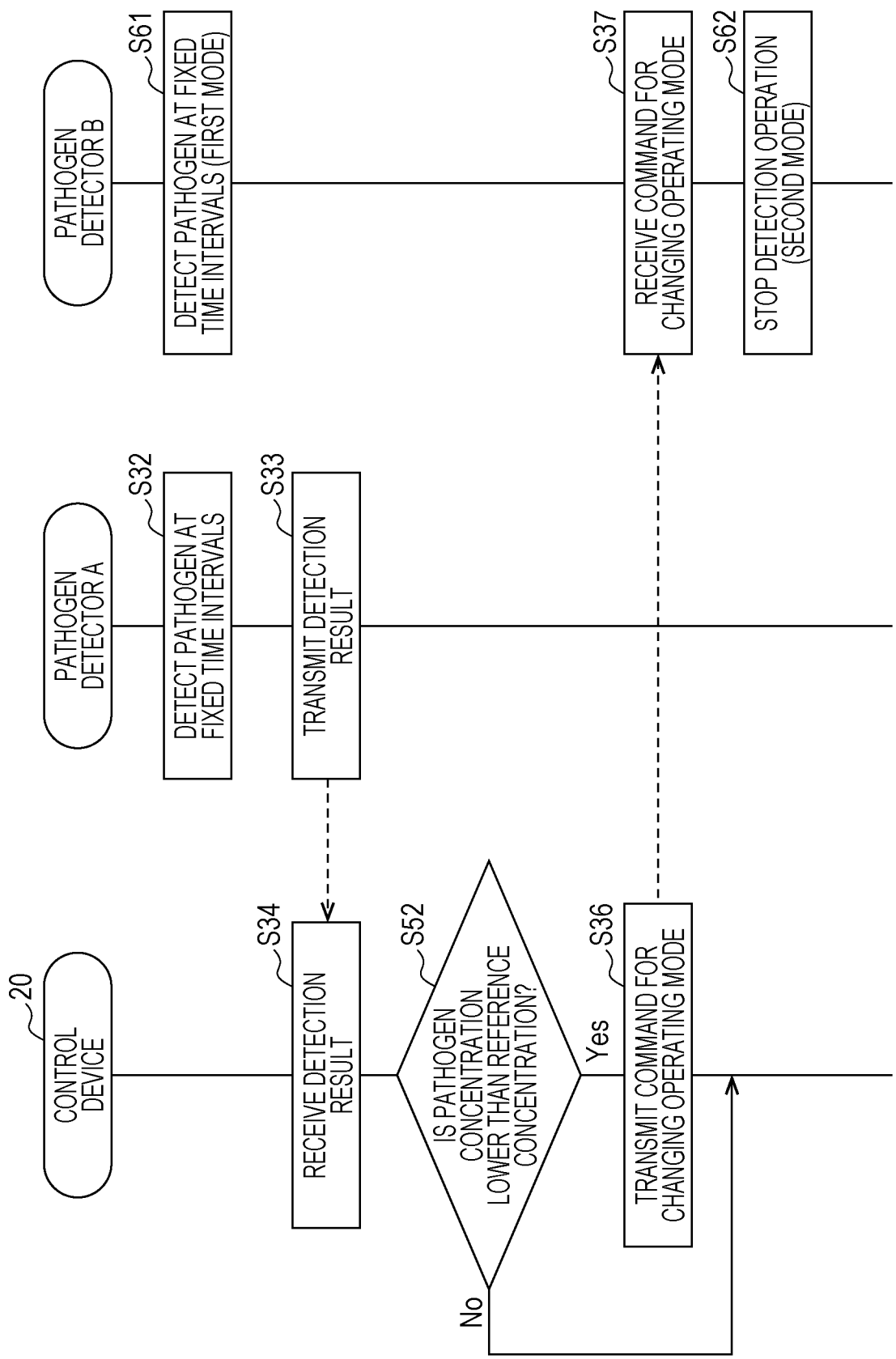

FIG. 15

| PATHOGEN DETECTOR ID | PATHOGEN CONCENTRATION | DETECTION TIME |
|---|---|---|
| 10c | 100 | 2017/8/3 13:30 |
| 10p | 90 | 2017/8/3 13:30 |
| 10n | 50 | 2017/8/3 13:30 |
| 10o | 80 | 2017/8/3 13:30 |
| 10m | 15 | 2017/8/3 13:30 |
| ... | ... | ... | ent 1;

PATHOGEN DETECTION SYSTEM AND PATHOGEN DETECTION METHOD

BACKGROUND

1. Technical Field

The present disclosure relates to a pathogen detection system that detects a pathogen such as a virus suspended in the air.

2. Description of the Related Art

To prevent the spread of infectious diseases such as influenza, technologies that detect pathogens such as viruses suspended in the air have been developed. Furthermore, technologies that provide mapping of how a pathogen spreads in a region in accordance with pathogen detection results have also been developed (for example, see Japanese Unexamined Patent Application Publication No. 2012-52866, Japanese Unexamined Patent Application Publication No. 2005-275708, and International Publication No. 2015/136695).

SUMMARY

One non-limiting and exemplary embodiment provides a pathogen detection system that detects pathogens efficiently.

In one general aspect, the techniques disclosed here feature a pathogen detection system including pathogen detectors disposed in different locations, and a controller. The pathogen detectors include a first pathogen detector and a second pathogen detector. The first pathogen detector transmits a first detection result obtained as a result of pathogen detection to the controller, and the second pathogen detector transmits a second detection result obtained as a result of pathogen detection to the controller. In a case where the first detection result satisfies a predetermined condition, the controller causes the second pathogen detector to change a mode related to the pathogen detection from a first mode to a second mode.

It should be noted that general or specific embodiments may be implemented as a system, a method, an integrated circuit, a computer program, a computer-readable storage medium, or any selective combination thereof. Computer-readable recording media include non-volatile recording media such as Compact Disc-Read-Only Memory (CD-ROM), for example.

According to the pathogen detection system of the present disclosure, improved efficiency in pathogen detection may be obtained. Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 6 is a table illustrating an example of detection results stored in a second storage;

FIG. 7 is a flowchart of a pathogen concentration detection operation by the pathogen detectors;

FIG. 8 is a diagram illustrating a communication sequence when an operating mode of the pathogen detectors is changed;

FIG. 9 is a diagram illustrating a sequence of Example 1 of changing the operating mode of the pathogen detectors in the pathogen detection system according to Embodiment 1;

FIG. 10 is a diagram illustrating a sequence of Example 2 of changing the operating mode of the pathogen detectors in the pathogen detection system according to Embodiment 1;

FIG. 11 is a diagram illustrating a sequence of Example 3 of changing the operating mode of the pathogen detectors in the pathogen detection system according to Embodiment 1;

FIG. 12 is a diagram illustrating a sequence of Example 4 of changing the operating mode of the pathogen detectors in the pathogen detection system according to Embodiment 1;

FIG. 15 is a table illustrating another example of detection results stored in the second storage;

Figure 1:
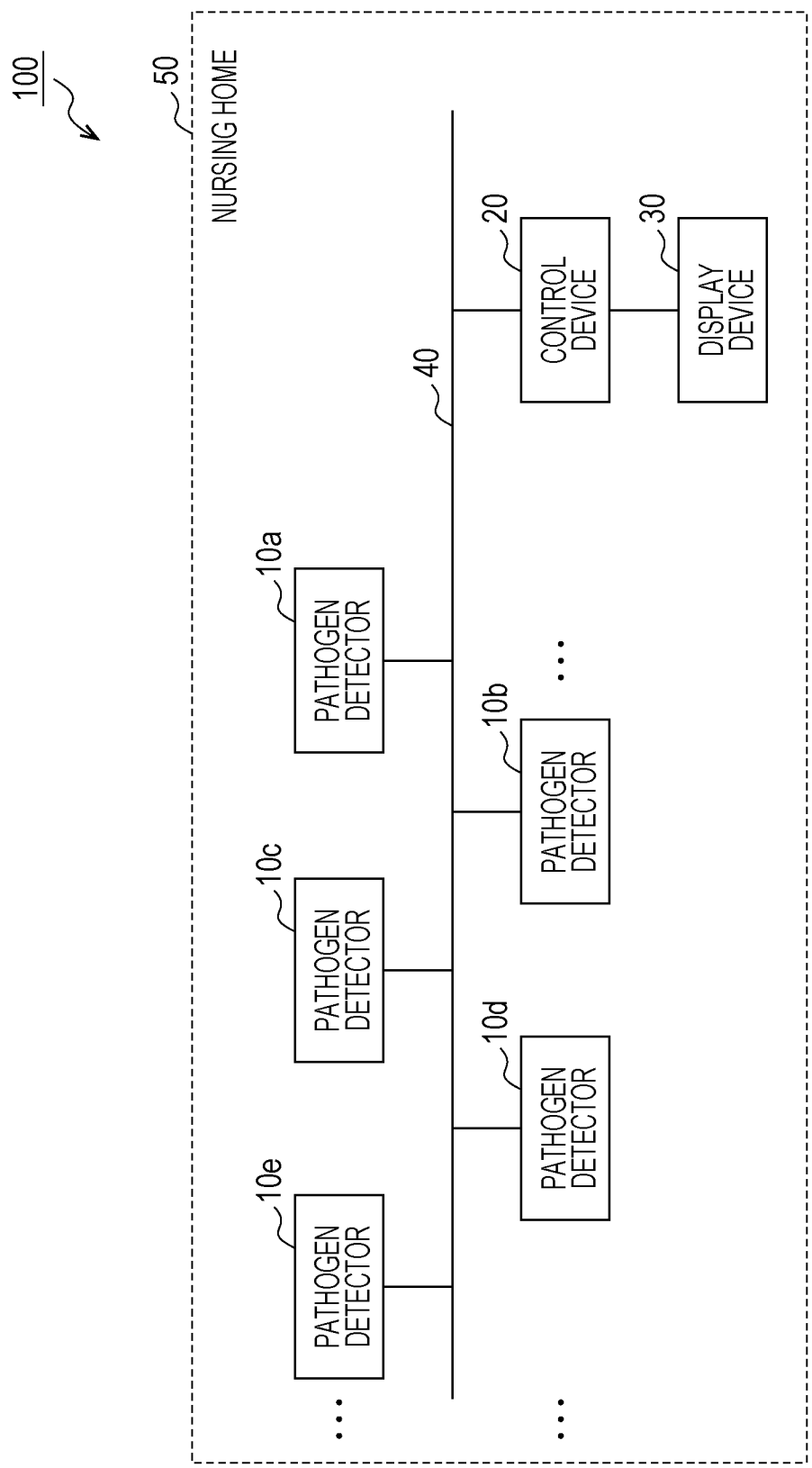
FIG. 1 is a block diagram illustrating an overall configuration of a pathogen detection system according to Embodiment 1.

DETAILED DESCRIPTION (Underlying Knowledge Forming Basis of the Present Disclosure)

To prevent the spread of infectious diseases such as influenza, technologies that detect pathogens such as viruses suspended in the air have been developed. Furthermore, technologies that provide mapping of how a pathogen spreads in a region in accordance with pathogen detection results have also been developed.

For example, Japanese Unexamined Patent Application Publication No. 2012-52866 discloses a technology that collects viruses suspended in the air to perform continuous and real-time monitoring of the status of virus presence.

Also, Japanese Unexamined Patent Application Publication No. 2005-275708 discloses a technology that uses a communication network to accumulate virus information obtained from mobile information terminals equipped with a virus detection function, and transmits information for preventing infectious diseases.

Furthermore, International Publication No. 2015/136695 discloses a technology that generates an infection spread map in accordance with detection data related to a pathogen acquired from detection devices capable of pathogen detection that are installed over a wide area and in places with many people, such as means of public transportation and schools.

Meanwhile, the season when an infectious disease spreads in a country is approximately the same season every year, and often lasts for several months. For example, in Japan, the season when influenza spreads approximately lasts from December to March.

Consequently, it is inefficient to cause all installed detectors to detect the pathogen throughout the year to grasp the spread of a specific infectious disease in a specific region, because such operation of the detectors may be highly wasteful.

On the other hand, pathogens are often brought in from infected regions outside the country, and if pathogen detection is not performed at all during times other than the anticipated infectious season in the country, the spread of an infectious disease cannot be grasped accurately.

Furthermore, in the case of using reagents such as antibodies for pathogen detection, because such reagents are consumables that are expended every time a detection is performed, there is demand to reduce the consumption of reagents by limiting pathogen detection as much as possible except for periods when pathogen detection is necessary.

A pathogen detection system according to an aspect of the present disclosure includes pathogen detectors disposed in different locations, and a controller. The pathogen detectors include a first pathogen detector and a second pathogen detector. The first pathogen detector transmits a first detection result obtained as a result of pathogen detection to the controller, and the second pathogen detector transmits a second detection result obtained as a result of pathogen detection to the controller. In a case where the first detection result satisfies a predetermined condition, the controller causes the second pathogen detector to change a mode related to the pathogen detection from a first mode to a second mode.

For example, the pathogen detection system changes the detection mode from the first mode to the second mode in accordance with the pathogen detection result. With this arrangement, the pathogen detection system may attain improved efficiency in pathogen detection. Also, the pathogen detection system may reduce the consumption of consumables such as a reagent used in pathogen detection.

Also, for example, the predetermined condition is that a pathogen concentration obtained as the first detection result is a predetermined reference concentration or higher.

The pathogen detection system is capable of changing the operating mode by treating the pathogen concentration being a reference concentration or higher as the predetermined condition.

Also, for example, in the first mode, the second pathogen detector detects a second pathogen concentration at first time intervals, while in the second mode, the second pathogen detector detects a third pathogen concentration at second time intervals, and each of the first time intervals is different from each of the second time intervals. The pathogen detection system is capable of changing the pathogen concentration detection frequency.

Also, for example, in the first mode, the second pathogen detector stops the pathogen detection, and in the second mode, the second pathogen detector performs the pathogen detection at fixed time intervals.

When the pathogen concentration detected by a first pathogen detector is the reference concentration or higher and there is great need to detect the pathogen concentration in a location other than where the first pathogen detector is installed, the pathogen detection system causes a second pathogen detector to detect the pathogen concentration. In other words, when there is little need to detect the pathogen concentration, the pathogen detection system causes the second pathogen detector to stop detecting the pathogen concentration. Consequently, the pathogen detection system is capable of efficiently detecting the pathogen concentration inside a building.

Also, for example, the first time interval is longer than the second time interval.

When the pathogen concentration detected by a first pathogen detector is the reference concentration or higher and there is great need to detect the pathogen concentration in a location other than where the first pathogen detector is installed, the pathogen detection system shortens the time interval of pathogen concentration detection by a second pathogen detector. In other words, when there is little need to detect the pathogen concentration, the pathogen detection system lowers the detection frequency of pathogen concentration detection by the second pathogen detector. Consequently, the pathogen detection system is capable of efficiently detecting the pathogen concentration inside a building.

Also, for example, the predetermined condition is that a pathogen concentration obtained as the first detection result is lower than a predetermined reference concentration.

The pathogen detection system is capable of changing the operating mode by treating the pathogen concentration being lower than a reference concentration as the predetermined condition.

Also, for example, in the first mode, the second pathogen detector performs the pathogen detection at fixed time intervals, and in the second mode, the second pathogen detector stops the pathogen detection.

When the pathogen concentration detected by a first pathogen detector is lower than the reference concentration and there is little need to detect the pathogen concentration in a location other than where the first pathogen detector is installed, the pathogen detection system causes a second pathogen detector to stop detecting the pathogen concentration. Consequently, the pathogen detection system is capable of efficiently detecting the pathogen concentration inside a building.

Also, for example, in the first mode, the second pathogen detector detects a second pathogen concentration at second time intervals, and in the second mode, the second pathogen detector detects a third pathogen concentration at first time intervals, each of the second time intervals being shorter than each of the first time intervals.

When the pathogen concentration detected by a first pathogen detector is the reference concentration or lower and there is little need to detect the pathogen concentration in a location other than where the first pathogen detector is installed, the pathogen detection system lengthens the time interval of pathogen concentration detection by a second pathogen detector. In other words, when there is little need to detect the pathogen concentration in a location other than where a first pathogen detector is installed, the pathogen detection system lowers the detection frequency of pathogen concentration detection by the second pathogen detector. Consequently, the pathogen detection system is capable of efficiently detecting the pathogen concentration inside a building.

Also, for example, the pathogen detection system further includes a storage. The storage stores information indicating a pathogen detector having a shortest pathogen transmission distance with respect to each of the pathogen detectors, the pathogen detector having the shortest transmission distance being included in the pathogen detectors. The pathogen detector having the shortest transmission distance with respect to the first pathogen detector is the second pathogen detector.

The pathogen detection system is capable of specifying, in accordance with the information, the pathogen detector whose operating mode is to be changed.

Also, for example, the transmission distance is determined in accordance with information about a layout of a building and information about the locations where the pathogen detectors are respectively installed.

The pathogen detection system is capable of generating table information in accordance with the building layout information and the pathogen detector positions.

Also, for example, the transmission distance is updated in accordance with pathogen concentration detection results detected by the pathogen detectors.

The pathogen detection system is capable of changing, in accordance with the pathogen concentration detected by the pathogen detector, the pathogen detector whose operating mode is to be changed.

Also, for example, the pathogen detection system further includes a display that displays information based on pathogen concentrations detected by the pathogen detectors.

The pathogen detection system is capable of displaying the pathogen concentration inside the building or the status of pathogen propagation inside the building. The user is able to grasp the pathogen concentration inside the building or the status of pathogen propagation inside the building.

Also, a pathogen detection method according to an aspect of the present disclosure includes: receiving pathogen detection results from pathogen detectors disposed in different locations, the pathogen detectors including a first pathogen detector and a second pathogen detector; and causing the second pathogen detector to change a mode related to pathogen detection from a first mode to a second mode in a case where a first pathogen detection result obtained by the first pathogen detector performing the pathogen detection satisfies a predetermined condition.

Note that these general or specific aspects may also be realized by a system, an apparatus, a method, an integrated circuit, a computer program, a computer-readable recording medium such as CD-ROM, or any selective combination thereof. For example, the present disclosure may also be realized as a pathogen detection method executed by a computer or the like as above. The present disclosure may be realized as a program for causing the computer to execute the pathogen detection method, or as a non-transitory computer-readable recording medium storing such a program.

Hereinafter, embodiments will be described specifically with reference to the drawings. Note that the embodiments described hereinafter all illustrate general or specific examples. Features such as numerical values, shapes, materials, structural elements, layout positions and connection states of structural elements, steps, and the ordering of steps indicated in the following embodiments are merely examples, and are not intended to limit the present disclosure. In addition, among the structural elements in the following embodiments, structural elements that are not described in the independent claims indicating the broadest concept are described as optional structural elements.

Note that each diagram is a schematic diagram, and does not necessarily illustrate a strict representation. Also, in each diagram, parts of the configuration which are essentially the same are denoted by the same signs, and duplicate description of such parts may be omitted or simplified in some cases.

Embodiment 1

[Configuration]

Figure 2:
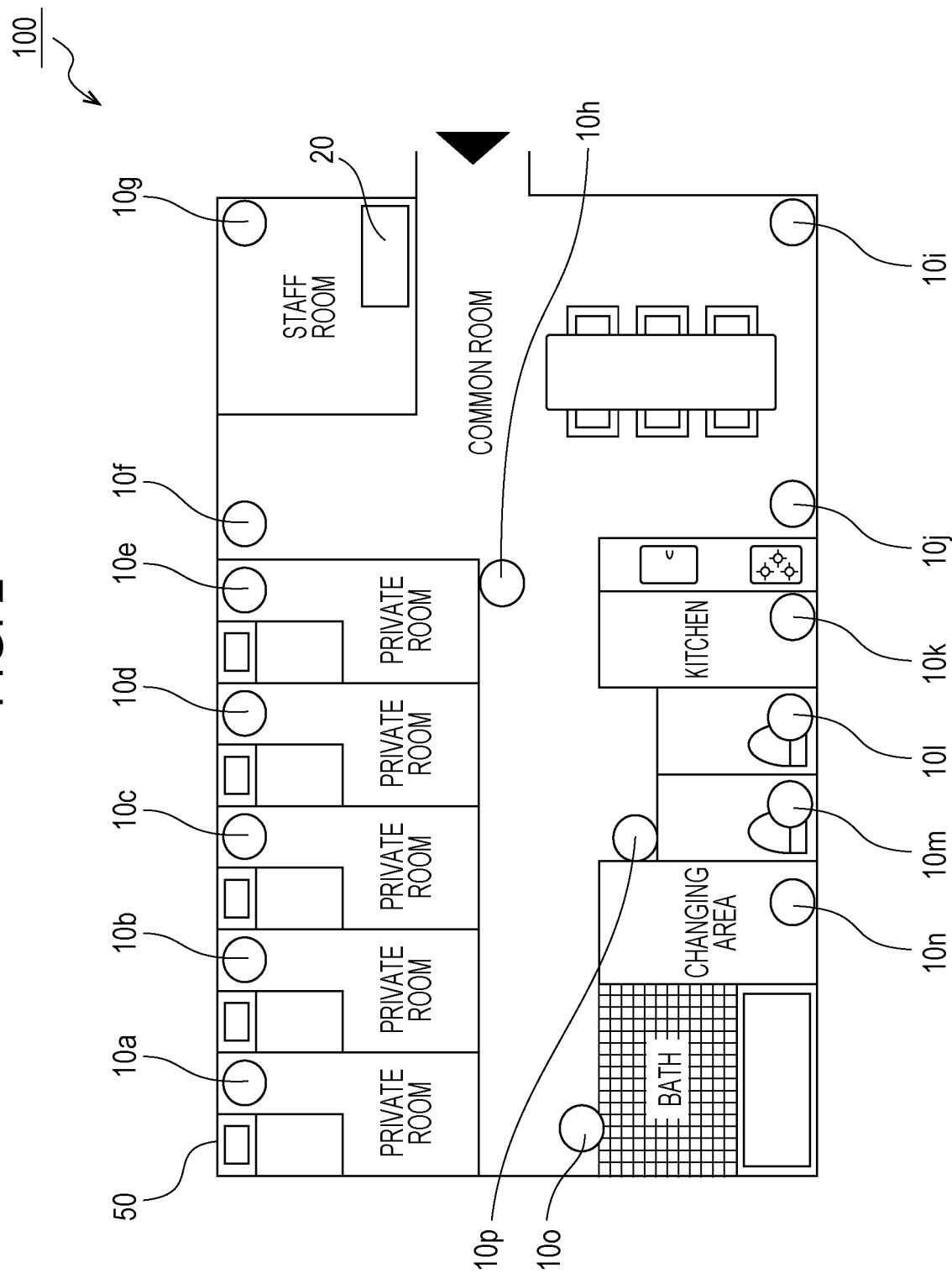
FIG. 2 is a diagram illustrating an arrangement of devices forming the pathogen detection system according to Embodiment 1.

Hereinafter, a configuration of a pathogen detection system according to Embodiment 1 will be described. FIG. 1 is a block diagram illustrating an overall configuration of the pathogen detection system according to Embodiment 1. FIG. 2 is a diagram illustrating an arrangement of devices forming the pathogen detection system according to Embodiment 1.

As illustrated in FIGS. 1 and 2, a pathogen detection system 100 according to Embodiment 1 is a system that is provided in a nursing home 50 and performs pathogen detection. In the present embodiment, pathogen detection detects the concentration of a pathogen present in the air inside the nursing home 50. The nursing home 50 is an example of a building.

The pathogen detection system 100 includes pathogen detectors 10a to 10p, a control device 20, and a display device 30. Note that it is sufficient for the pathogen detection system 100 to include at least two pathogen detectors, and the number of pathogen detectors provided in the pathogen detection system 100 is not particularly limited.

Each of the pathogen detectors 10a to 10p performs an operation for detecting the pathogen concentration at fixed time intervals, for example. The pathogen is a virus such as the influenza virus, for example, but may also be mold or bacteria.

The pathogen detectors 10a to 10p are installed in different locations inside the nursing home 50. For example, the pathogen detectors 10a to 10e are respectively installed in private rooms. The pathogen detectors 10f, 10h, 10o, and 10p are installed in a hallway. The pathogen detector 10g is installed in a staff room. The pathogen detectors 10i and 10j are installed in a common room. The pathogen detector 10k is installed in a kitchen. The pathogen detectors 10l and 10m are respectively installed in bathrooms. The pathogen detector 10n is installed in a changing area.

The pathogen detectors 10a to 10p are connected to the control device 20 installed in the staff room by a communication network 40. The communication network 40 is a local area network (LAN), for example. The communication network 40 may be a wired communication network or a wireless communication network.

Figure 3:
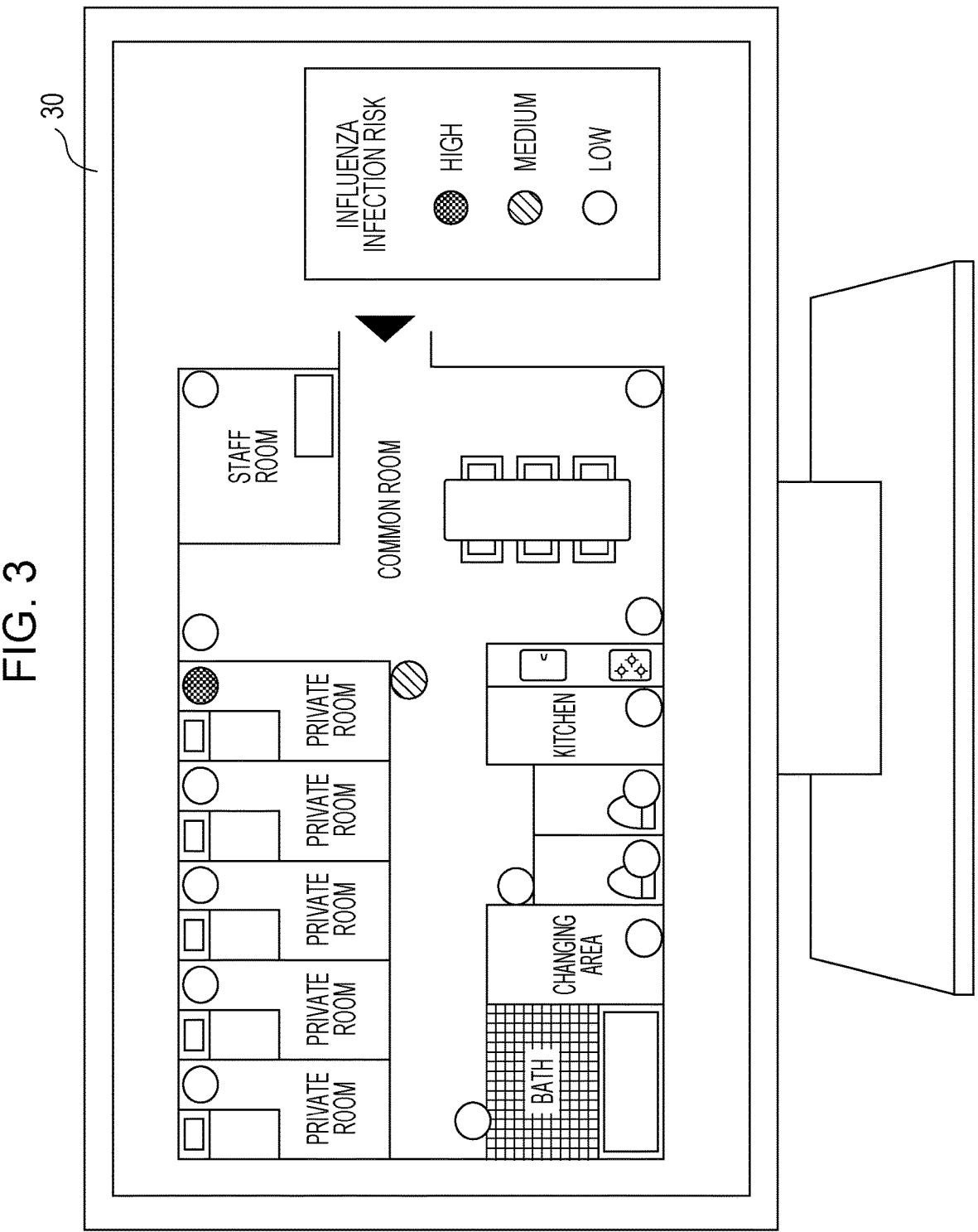
FIG. 3 is a diagram illustrating an example of an image displayed on a display device.

Each of the pathogen detectors 10a to 10p transmits a detection result to the control device 20 over the communication network 40. The detection results will be described later in detail. The control device 20 stores the acquired detection results, and in accordance with the stored detection results, causes the display device 30 to display an image based on the pathogen concentrations in the air surrounding the pathogen detectors 10a to 10p installed inside the nursing home 50. FIG. 3 is a diagram illustrating an example of an image displayed on the display device 30. In FIG. 3, a "high influenza infection risk" means a "high pathogen concentration", a "medium influenza infection risk" means a "medium pathogen concentration", and a "low influenza infection risk" means a "low pathogen concentration". According to the image as illustrated in FIG. 3, a person such as a staff member of the nursing home 50 is able to grasp the distribution of pathogen concentrations in the air and the status of pathogen propagation inside the nursing home 50. In other words, the pathogen detection system 100 also functions as a propagation status monitoring system for monitoring the status of pathogen propagation.

Also, the control device 20 controls the time intervals at which the pathogen detectors 10a to 10p detect the pathogen concentration. In other words, the control device 20 controls the time intervals at which the pathogen detectors 10a to 10p detect the pathogen concentration. Specifically, by transmitting a command for changing the operating mode for detecting the pathogen concentration, the control device 20 causes the pathogen concentration to be detected at shorter time intervals in pathogen detectors where the probability of the pathogen being present nearby is estimated to be higher. With this arrangement, efficient detection of the pathogen is achieved. Such changing of the operating mode (in other words, control of the detection time intervals) will be described later in detail.

[Pathogen Detector]

Figure 4:
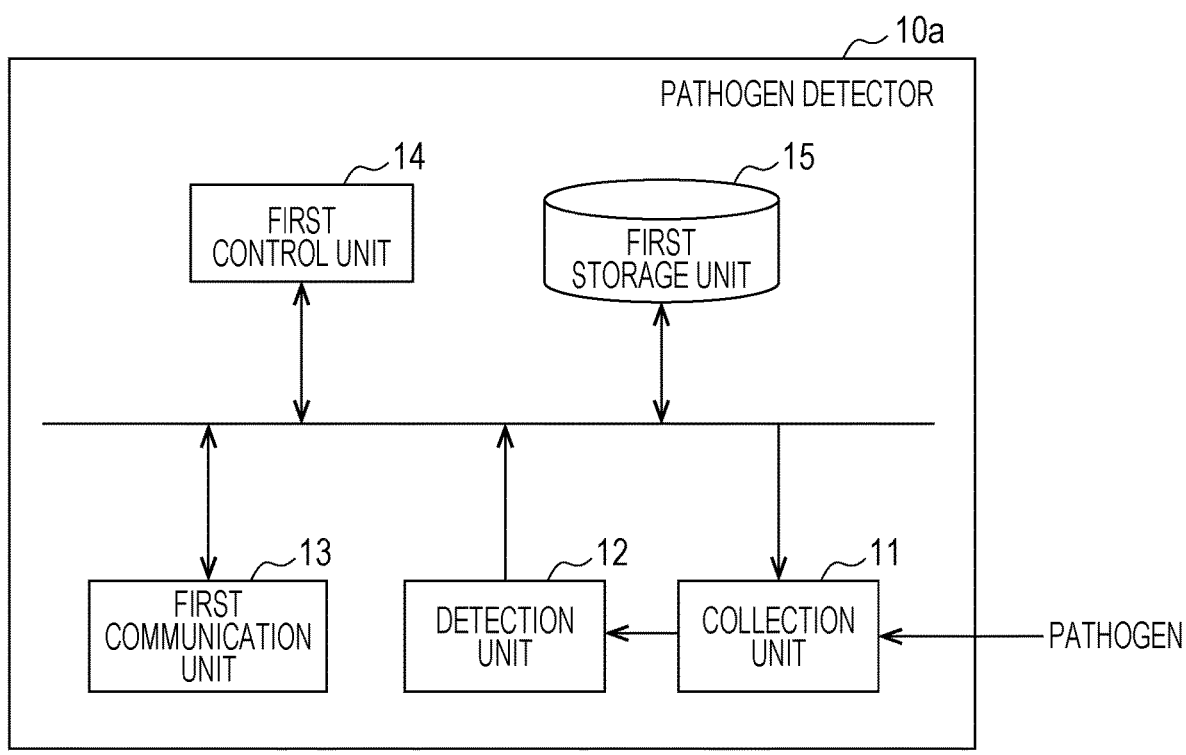
FIG. 4 is a block diagram illustrating a functional configuration of a pathogen detector.

Next, a detailed configuration of each device included in the pathogen detection system 100 will be described. First, a functional configuration of the pathogen detector 10a will be described. FIG. 4 is a block diagram illustrating a functional configuration of the pathogen detector 10a. Note that because the other pathogen detectors provided in the pathogen detection system 100 have a configuration similar to the pathogen detector 10a, a detailed description thereof is omitted.

The pathogen detector 10a performs an operation for detecting the concentration of a pathogen included among microparticles in the surrounding air. As illustrated in FIG. 4, the pathogen detector 10a includes a collection unit 11, a detection unit 12, a first communication unit 13, a first control unit 14, and a first storage unit 15.

The collection unit 11 sucks in and collects microparticles suspended in the air. Specifically, the collection unit 11 includes a fan or pump for intake, for example, and collects microparticles in intake air entering from an intake port.

The detection unit 12 detects the pathogen concentration. For example, the detection unit 12 is a sensor that uses detection technology utilizing surface plasmon field-enhanced fluorescence spectroscopy or the like to detect the concentration of a pathogen in the microparticles collected by the collection unit 11. The detection unit 12 is also capable of detecting the pathogen concentration. The method of detecting the pathogen concentration will be described later.

The first communication unit 13 communicates with the control device 20. For example, the first communication unit 13 transmits the detection result from the pathogen detector 10a to the control device 20 under control by the first control unit 14. Specifically, the first communication unit 13 is a communication circuit capable of performing communication over the communication network 40.

The first control unit 14 is a control device that controls units such as the collection unit 11, the detection unit 12, and the first communication unit 13. The first control unit 14 generates a detection result, which is information including an ID of the pathogen detector 10a, the pathogen concentration detected by the detection unit 12, and a detection time indicating when the pathogen detector 10a detected the pathogen concentration. The first control unit 14 is realized by a device such as a microcontroller for example, but may also be realized by a processor or a dedicated circuit.

The first storage unit 15 is a storage device that stores a control program executed by the first control unit 14. Specifically, the first storage unit 15 is realized by a device such as semiconductor memory.

[Control Device and Display Device]

Figure 5:
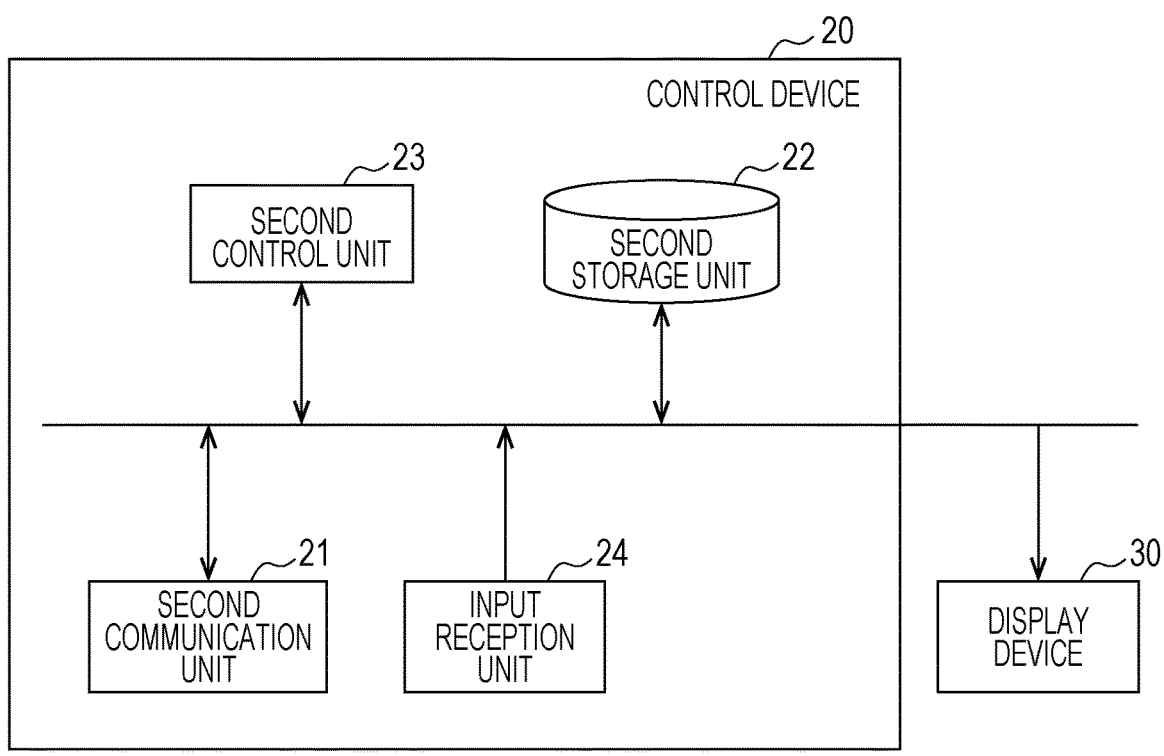
FIG. 5 is a block diagram illustrating a functional configuration of a control device.

Next, a functional configuration of the control device 20 will be described. FIG. 5 is a block diagram illustrating a functional configuration of the control device 20. Note that in FIG. 5, the display device 30 is also illustrated.

The control device 20 controls the pathogen detectors 10a to 10p disposed in different locations inside the nursing home 50. The control device 20 is an information communication terminal such as a personal computer or a server, for example. As illustrated in FIG. 5, the control device 20 includes a second communication unit 21, a second storage unit 22, a second control unit 23, and an input reception unit 24.

The second communication unit 21 communicates with the pathogen detectors 10a to 10p. For example, the second communication unit 21 receives a detection result transmitted from each of the pathogen detectors 10a to 10p. Also, the second communication unit 21 transmits a command for changing the operating mode of the pathogen detectors 10a to 10p under control by the second control unit 23. Specifically, the second communication unit 21 is a communication circuit capable of performing communication over the communication network 40.

The second storage unit 22 stores the respective detection results from the pathogen detectors 10a to 10p received by the second communication unit 21. FIG. 6 is a table illustrating an example of the detection results stored in the second storage unit 22. As illustrated in FIG. 6, each detection result from the pathogen detectors 10a to 10p includes a pathogen detector ID, a pathogen concentration, and a detection time indicating when the pathogen concentration was detected. The pathogen detector IDs of the pathogen detectors 10a to 10p are "10a" to "10p", respectively. Additionally, the second storage unit 22 also stores information such as table information indicating correspondence relationships among the pathogen detectors 10a to 10p described later, and the control program executed by the second control unit 23. Specifically, the second storage unit 22 is realized by a device such as semiconductor memory.

The second control unit 23 is a control device that controls units such as the second communication unit 21. For example, the second control unit 23 controls the operating mode of at least some of the pathogen detectors 10a to 10p by causing the second communication unit 21 to transmit the command for changing the operating mode. The second control unit 23 also performs processes such as a process of storing detection results in the second storage unit 22 and an image display process that causes the display device 30 to display an image in accordance with a user operation received by the input reception unit 24. The second control unit 23 is realized by a device such as a microcontroller for example, but may also be realized by a processor or a dedicated circuit.

The input reception unit 24 is a user interface device that receives user operations related to the pathogen concentration detection by the pathogen detectors 10a to 10p. For example, the input reception unit 24 receives a user operation for displaying an image like the one illustrated in FIG. 3. Specifically, the input reception unit 24 is an input device such as a mouse or a keyboard.

The display device 30 displays the pathogen concentrations detected by the pathogen detectors 10a to 10p under control by the second control unit 23. The display device 30 may also display an image based on the detected pathogen concentrations like the one illustrated in FIG. 3, for example. The display device 30 is realized by a display panel such as a liquid crystal panel or an organic electroluminescence (EL) panel.

[Pathogen Concentration Detection Operation by Pathogen Detector]

Next, a pathogen concentration detection operation by the pathogen detector 10a will be described. FIG. 7 is a flowchart of a pathogen concentration detection operation by the pathogen detector 10a.

First, the collection unit 11 collects microparticles in the air with a fan or pump for intake (S11). Next, the detection unit 12 separates the suctioned microparticles from the air (S12). The detection unit 12 has a cyclone structure, for example, and utilizes centrifugal force to separate pathogen-containing microparticles from the air. The microparticles contain the pathogen.

Next, the detection unit 12 extract the pathogen from the separated microparticles (S13). Specifically, after mixing the separated microparticles with a solvent that dissolves the pathogen well, the detection unit 12 generates an extraction fluid. In this way, the pathogen is extracted from the microparticles.

Subsequently, the detection unit 12 introduces a sample fluid acquired from the extraction fluid into a metal microstructure affixed with an antibody that bonds specifically with the pathogen. Furthermore, the detection unit 12 introduces an antibody that bonds specifically with the pathogen and is also labeled by a fluorescent substance into the metal microstructure (S14). In this way, the pathogen in the sample fluid bonds with the metal microstructure via the antibody, and also bonds with the antibody labeled by the fluorescent substance.

Next, the detection unit 12 irradiates the metal microstructure with excitation light from a light source included in the detection unit 12 (S15). In this way, surface-enhanced fluorescence corresponding to the quantity of pathogen is emitted by surface plasmons produced on the metal microstructure. A photodetector included in the detection unit 12 detects such fluorescence, and the detection unit 12 can detect the pathogen concentration in the sample fluid in accordance with the intensity of the fluorescence. The pathogen concentration in the air near the pathogen detector 10a can be determined from the concentration of the pathogen in the sample fluid and the quantity of intake air drawn into the collection unit 11.

Note that in the following Embodiment 1, the detection operation in FIG. 7 is also simply referred to as "detection". For example, "detection is performed at fixed time intervals" means that the detection operation illustrated in the flowchart of FIG. 7 is performed at fixed time intervals. Herein, a "time interval" corresponds to the amount of time between the start time of the step of collecting microparticles (S11) in the detection operation of FIG. 7 and the start time of the step of collecting microparticles (S11) in the next detection operation. The detection time indicating when the pathogen concentration was detected, which is included in each detection result, may be the start time of the step of collecting microparticles (S11).

[Example 1 of Changing Operating Mode]

Next, Example 1 of changing the operating mode of the pathogen detectors will be described. First, a communication sequence when the operating mode is changed will be described. FIG. 8 is a diagram illustrating a communication sequence when an operating mode of the pathogen detectors is changed. Note that in the following description of changing the operating mode, an example will be described in which a detection result from one pathogen detector A among the pathogen detectors 10a to 10p is used as the basis for changing the operating mode of another pathogen detector B among the pathogen detectors 10a to 10p.

As illustrated in FIG. 8, the pathogen detector A and the pathogen detector B initially operate in a first mode. The pathogen detector A and the pathogen detector B operating in the first mode detect the pathogen concentration at first time intervals T1, and transmit detection results to the control device 20 every time detection is performed (S21). When the control device 20 determines that the pathogen concentration included in the detection result received from the pathogen detector A satisfies a predetermined condition, the control device 20 transmits a command for changing the operating mode to the pathogen detector B (S22). Note that in the example of FIG. 8, the control device 20 also transmits the command for changing the operating mode to the pathogen detector A, but it is sufficient to transmit the command for changing the operating mode to at least the pathogen detector B.

Each of the pathogen detector A and the pathogen detector B receives the command for changing the operating mode and changes the operating mode from the first mode to a second mode. Each of the pathogen detector A and the pathogen detector B operating in the second mode detects the pathogen concentration at second time intervals T2 each of which is shorter than each of the first time intervals T1 (S23). In other words, the time interval for detecting the pathogen concentration in the first mode is different from the time interval for detecting the pathogen concentration in the second mode.

Next, Example 1 of changing the operating mode will be described in detail. FIG. 9 is a diagram illustrating a sequence of Example 1 of changing the operating mode of the pathogen detector B in the pathogen detection system 100.

In FIG. 9, the pathogen detector B is operating in the first mode. The first mode is the mode in which the pathogen concentration is detected at the first time intervals T1. In other words, the detection unit 12 of the pathogen detector B operating in the first mode is detecting the pathogen concentration at the first time intervals T1 (S31).

Meanwhile, the detection unit 12 of the pathogen detector A is detecting the pathogen concentration at fixed time intervals (S32). In step S32, the pathogen detector A operates in the first mode like in FIG. 8, for example. In other words, the detection unit 12 of the pathogen detector A detects the pathogen concentration at the first time intervals T1. In step S32, the detection unit 12 of the pathogen detector A may be detecting the pathogen concentration at time intervals other than the first time intervals T1.

In this case, the first communication unit 13 of the pathogen detector A transmits a detection result including the pathogen concentration detected by the detection unit 12 at the fixed time intervals to the control device 20 (S33). The second communication unit 21 of the control device 20 receives the detection result of the pathogen detector A from the first communication unit 13 of the pathogen detector A (S34).

The second control unit 23 of the control device 20 determines whether or not the pathogen concentration included in the detection result from the pathogen detector A satisfies a predetermined condition. Specifically, the predetermined condition is that the pathogen concentration is a predetermined reference concentration or higher. In other words, the second control unit 23 determines whether or not the pathogen concentration detected by the pathogen detector A is the predetermined reference concentration or higher (S35).

In the case where the pathogen concentration detected by the pathogen detector A is determined to be lower than the predetermined reference concentration (S35, No), the operating mode of the pathogen detector B is not changed. On the other hand, in the case where the pathogen concentration detected by the pathogen detector A is determined to be the predetermined reference concentration or higher (S35, Yes), the second control unit 23 causes the second communication unit 21 to transmit the command for changing the operating mode (S36). Specifically, the command for changing the operating mode is a command indicating a change to the second mode. In other words, the second control unit 23 commands the pathogen detector B to change the operating mode for detecting the pathogen concentration from the first mode to the second mode. The second mode is a mode in which the pathogen concentration is detected at the second time intervals T2 each of which is shorter than each of the first time intervals T1.

The first communication unit 13 of the pathogen detector B receives the command for changing the operating mode (S37). When the pathogen detector B receives the command for changing the operating mode, the pathogen detector B starts operating in the second mode. Specifically, the first control unit 14 of the pathogen detector B causes the detection unit 12 of the pathogen detector B to detect the pathogen concentration at the second time intervals T2 (S38).

According to Example 1 of changing the operating mode, when the pathogen concentration detected by the pathogen detector A is the reference concentration or higher and there is great need to detect the pathogen concentration, the time interval of pathogen concentration detection by the pathogen detector B is shortened. In other words, when there is little need to detect the pathogen concentration, the detection frequency of pathogen concentration detection by some of the pathogen detectors is lowered. Consequently, the pathogen detection system 100 is capable of efficiently detecting the pathogen concentration in the air inside the nursing home 50.

[Example 2 of Changing Operating Mode]

Next, Example 2 of changing the operating mode of the pathogen detectors will be described. FIG. 10 is a diagram illustrating a sequence of Example 2 of changing the operating mode of the pathogen detectors in the pathogen detection system 100. Note that, unlike Example 1, in the following description of Example 2, the first mode is a mode in which the pathogen concentration detection is stopped, and the second mode is a mode in which the pathogen concentration detection is performed at fixed time intervals. Also, the following mostly describes the differences from Example 1 of changing the operating mode of the pathogen detectors, and a description of matters that have already been explained is omitted or simplified appropriately.

In FIG. 10, the pathogen detector B is operating in the first mode, where the detection operation has been stopped (S41). The detection unit 12 of the pathogen detector A is detecting the pathogen concentration at the fixed time intervals (S32). The first communication unit 13 of the pathogen detector A transmits a detection result including the pathogen concentration detected by the detection unit 12 at the fixed time intervals to the control device 20 (S33). The second communication unit 21 of the control device 20 receives the detection result of the pathogen detector A from the first communication unit 13 of the pathogen detector A (S34), and the second control unit 23 determines whether or not the pathogen concentration detected by the pathogen detector A is the predetermined reference concentration or higher (S35).

In the case where the pathogen concentration detected by the pathogen detector A is determined to be the predetermined reference concentration or higher (S35, Yes), the second control unit 23 causes the second communication unit 21 to transmit the command for changing the operating mode (S36).

The first communication unit 13 of the pathogen detector B receives the command for changing the operating mode (S37). When the command for changing the operating mode is received, the first control unit 14 of the pathogen detector B operates in the second mode, and causes the detection unit 12 of the pathogen detector B to start the pathogen concentration detection at fixed time intervals (S42).

According to Example 2 of changing the operating mode, when the pathogen concentration detected by the pathogen detector A is the reference concentration or higher and there is great need to detect the pathogen concentration, the pathogen detector B starts detecting the pathogen concentration. In other words, when there is little need to detect the pathogen concentration, the pathogen concentration detection by some of the pathogen detectors is stopped. Consequently, the pathogen detection system 100 is capable of efficiently detecting the pathogen concentration in the air inside the nursing home 50.

[Example 3 of Changing Operating Mode]

Next, Example 3 of changing the operating mode of the pathogen detectors will be described. FIG. 11 is a diagram illustrating a sequence of Example 3 of changing the operating mode of the pathogen detectors in the pathogen detection system 100. Note that in the following description of Example 3, the first mode is a mode in which the pathogen concentration detection is performed at the second time intervals T2, and the second mode is a mode in which the pathogen concentration detection is performed at the first time intervals T1 each of which is longer than each of the second time intervals T2. Also, the following mostly describes the differences from Example 1 of changing the operating mode of the pathogen detectors, and a description of matters that have already been explained is omitted or simplified appropriately.

In FIG. 11, the pathogen detector B is operating in the first mode, and the detection unit 12 of the pathogen detector B is detecting the pathogen concentration at the second time intervals T2 (S51). The detection unit 12 of the pathogen detector A is detecting the pathogen concentration at the fixed time intervals (S32). In step S32, the pathogen detector A is operating in the first mode, for example, and the detection unit 12 of the pathogen detector A detects the pathogen concentration at the second time intervals T2. In step S32, the detection unit 12 of the pathogen detector A may be detecting the pathogen concentration at time intervals other than the second time intervals T2.

In this case, the first communication unit 13 of the pathogen detector A transmits a detection result including the pathogen concentration detected by the detection unit 12 at the fixed time intervals to the control device 20 (S33). The second communication unit 21 of the control device 20 receives the detection result of the pathogen detector A from the first communication unit 13 of the pathogen detector A (S34).

The second control unit 23 of the control device 20 determines whether or not the pathogen concentration detected by the pathogen detector A satisfies a predetermined condition. Specifically, the predetermined condition is that the pathogen concentration is lower than a predetermined reference concentration. In other words, the second control unit 23 determines whether or not the pathogen concentration detected by the pathogen detector A is lower than the predetermined reference concentration (S52).

In the case where the pathogen concentration detected by the pathogen detector A is determined to be the predetermined reference concentration or higher (S52, No), the operating mode of the pathogen detector B is not changed. On the other hand, in the case where the pathogen concentration detected by the pathogen detector A is determined to be lower than the predetermined reference concentration (S52, Yes), the second control unit 23 causes the second communication unit 21 to transmit the command for changing the operating mode (S36).

The first communication unit 13 of the pathogen detector B receives the command for changing the operating mode (S37). When the pathogen detector B receives the command for changing the operating mode, the pathogen detector B starts operating in the second mode. Specifically, the first control unit 14 of the pathogen detector B causes the detection unit 12 of the pathogen detector B to detect the pathogen concentration at the first time intervals T1 (S53).

According to Example 3 of changing the operating mode, when the pathogen concentration detected by the pathogen detector A is lower than the reference concentration and there is little need to detect the pathogen concentration, the time interval of pathogen concentration detection by the pathogen detector B is lengthened. In other words, when there is little need to detect the pathogen concentration, the detection frequency of pathogen concentration detection by some of the pathogen detectors is lowered. Consequently, the pathogen detection system 100 is capable of efficiently detecting the pathogen concentration in the air inside the nursing home 50.

[Example 4 of Changing Operating Mode]

Next, Example 4 of changing the operating mode of the pathogen detectors will be described. FIG. 12 is a diagram illustrating a sequence of Example 4 of changing the operating mode of the pathogen detectors in the pathogen detection system 100. Note that in the following description of Example 4, the first mode is a mode in which the pathogen concentration detection is performed at fixed time intervals, and the second mode is a mode in which the detection is stopped. Also, the following mostly describes the differences from Example 3 of changing the operating mode of the pathogen detectors, and a description of matters that have already been explained is omitted or simplified appropriately.

In FIG. 12, the pathogen detector B is operating in the first mode, and is detecting the pathogen concentration at fixed time intervals (S61). The detection unit 12 of the pathogen detector A is detecting the pathogen concentration at fixed time intervals (S32). The first communication unit 13 of the pathogen detector A transmits a detection result including the pathogen concentration detected by the detection unit 12 at the fixed time intervals to the control device 20 (S33). The second communication unit 21 of the control device 20 receives the detection result of the pathogen detector A from the first communication unit 13 of the pathogen detector A (S34), and the second control unit 23 determines whether or not the pathogen concentration detected by the pathogen detector A is lower than the predetermined reference concentration (S52).

In the case where the pathogen concentration detected by the pathogen detector A is determined to be lower than the predetermined reference concentration (S52, Yes), the second control unit 23 causes the second communication unit 21 to transmit the command for changing the operating mode (S36).

The first communication unit 13 of the pathogen detector B receives the command for changing the operating mode (S37). When the command for changing the operating mode is received, the first control unit 14 of the pathogen detector B operates in the second mode, and causes the detection unit 12 of the pathogen detector B to stop the pathogen concentration detection (S62).

According to Example 4 of changing the operating mode, when the pathogen concentration detected by the pathogen detector A is lower than the reference concentration and there is little need to detect the pathogen concentration, the pathogen detector B stops detecting the pathogen concentration. Consequently, the pathogen detection system 100 is capable of efficiently detecting the pathogen concentration in the air inside the nursing home 50.

[Pathogen Detectors Subjected to Change of Operating Mode]

Figure 13A:
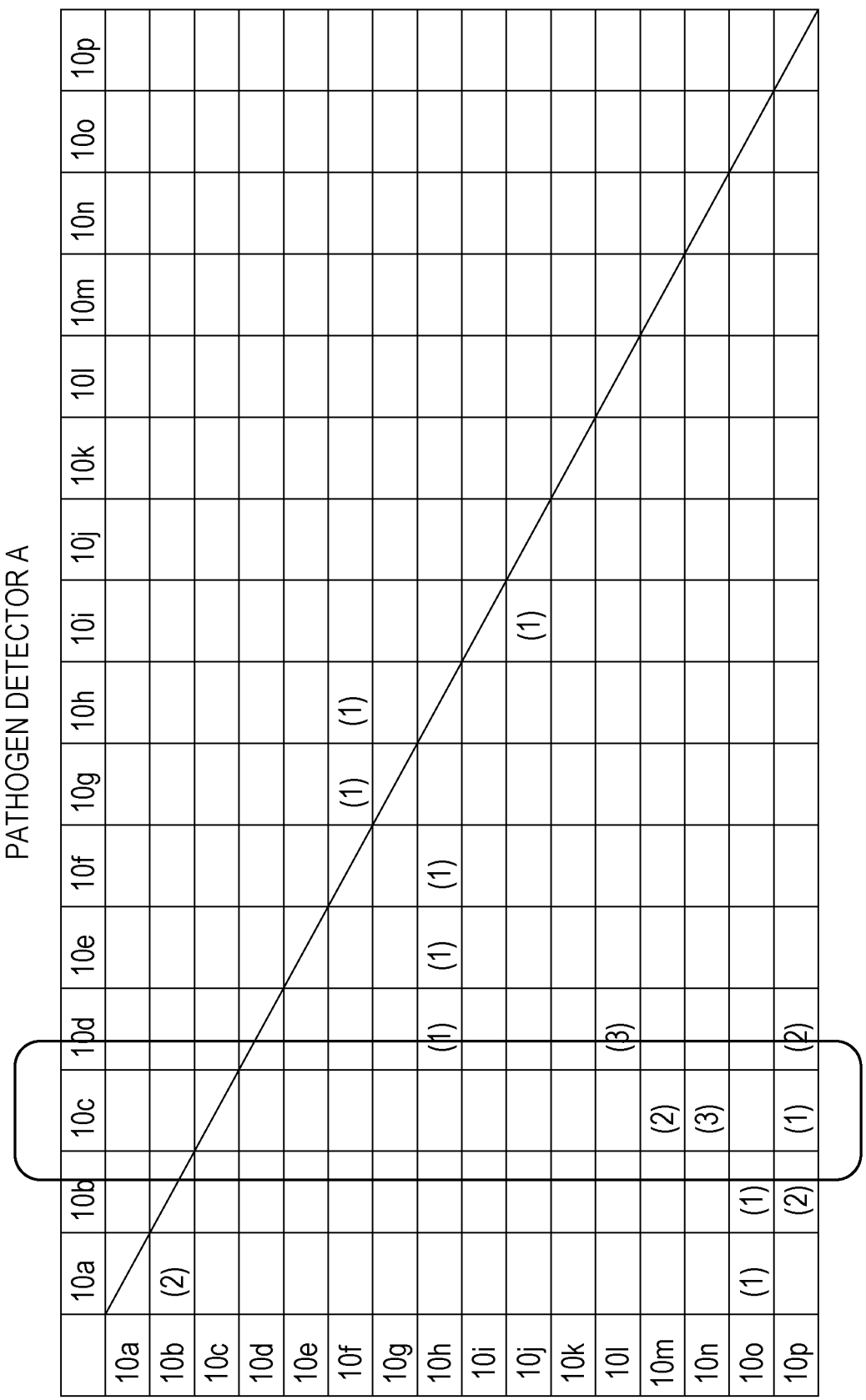
FIG. 13A is a diagram illustrating an example of table information.

Meanwhile, when the operating mode is changed, which of the pathogen detectors 10a to 10p is to be treated as the pathogen detector A and which is to be treated as the pathogen detector B are determined in accordance with the table information stored in the second storage unit 22, for example. FIG. 13A illustrates an example of the table information.

As illustrated in FIG. 13A, the table information expresses correspondence relationships among the pathogen detectors 10a to 10p. For example, the correspondence relationships expressed by the table information are determined in accordance with the positions of the pathogen detectors 10a to 10p.

Figure 13B:
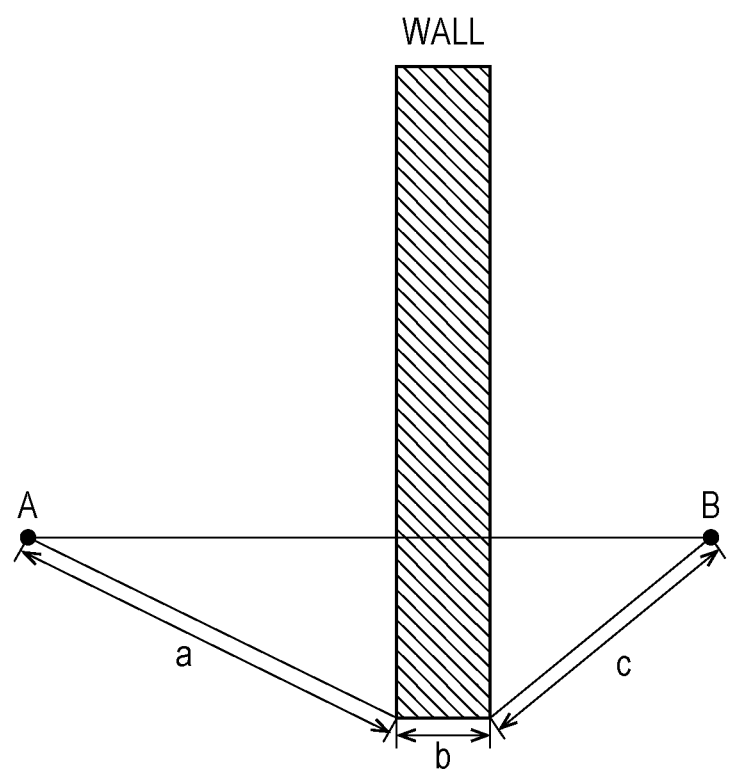
FIG. 13B is a diagram for explaining a pathogen propagation path length between two points.

For example, the correspondence relationships are determined in accordance with the lengths of propagation paths of the pathogen in the space inside the nursing home 50. A propagation path means the distance that the pathogen moves when propagating, or in other words, the spatial distance considering obstacles such as walls inside the nursing home 50. For example, as illustrated in FIG. 13B, if an obstacle such as a wall exists on a line segment joining points A and B, the length of the propagation path between the points A and B is (a+b+c). In other words, the correspondence relationships expressed by the table information are determined in accordance with information about the layout of the nursing home 50 and information about the locations where the pathogen detectors 10a to 10p are respectively disposed. The numerical values in the table information indicate the rank of the propagation path lengths, with a smaller number indicating a shorter propagation path. In other words, the numerical values in the table information indicate a ranking from the shortest propagation path. Note that each of the rooms where the pathogen detectors 10a to 10e, 10g, and 10k to 10n are installed has a door (not illustrated) capable of isolating the room from the other space. In the case of determining the distance moved when the pathogen propagates, the doors do not have to be considered as obstacles.

For example, as illustrated with the portion enclosed by the solid line in FIG. 13A, in the case where the pathogen detector 10c is used as the pathogen detector A, the pathogen detector having the shortest propagation path from the pathogen detector 10c is the pathogen detector 10p corresponding to the row containing (1) in the column corresponding to the pathogen detector 10c. The pathogen detector having the second-shortest propagation path from the pathogen detector 10c is the pathogen detector 10m corresponding to the row containing (2) in the column corresponding to the pathogen detector 10c. The pathogen detector having the third-shortest propagation path from the pathogen detector 10c is the pathogen detector 10n corresponding to the row containing (3) in the column corresponding to the pathogen detector 10c.

Note that in FIG. 13A, the notation of numerical values in the table is omitted for the cases where the pathogen detectors 10j to 10p are used as the pathogen detector A.

In the case where the pathogen concentration detected by one pathogen detector A satisfies a predetermined condition, the second control unit 23 issues a command to another pathogen detector B specified in accordance with such table information. For example, in the case where the pathogen concentration detected by the pathogen detector 10c satisfies the predetermined condition, the second control unit 23 issues the command for changing the operating mode to the pathogen detector 10p having the shortest propagation path from the pathogen detector 10c, and does not issue the command for changing the operating mode to other pathogen detectors.

Note that the second control unit 23 may also specify a predetermined number of pathogen detectors in order of shortest propagation path, and issue the command for changing the operating mode to the specified predetermined number of pathogen detectors. The above predetermined number may be three, for instance, and in the above example, the second control unit 23 may issue the command for changing the operating mode to three pathogen detectors, namely the pathogen detector 10p, the pathogen detector 10m, and the pathogen detector 10n.

In this case, the second control unit 23 uses the second communication unit 21 to transmit the command for changing the operating mode to the three pathogen detectors 10p, 10m, and 10n at substantially the same time, for example. Alternatively, the second control unit 23 may use the second communication unit 21 to transmit the command for changing the operating mode to the three pathogen detectors 10p, 10m, and 10n in this order, for example. In this case, the command for changing the operating mode is successively transmitted at roughly the same time intervals as the first time intervals T1 or the second time intervals T2, for example.

[Updating Table Information]

Note that the correspondence relationships expressed by the table information may be fixed, or may be changed (in other words, updated). For example, the correspondence relationships expressed by the table information may be updated in accordance with the detection results from the pathogen detectors 10a to 10p.

Figure 14:
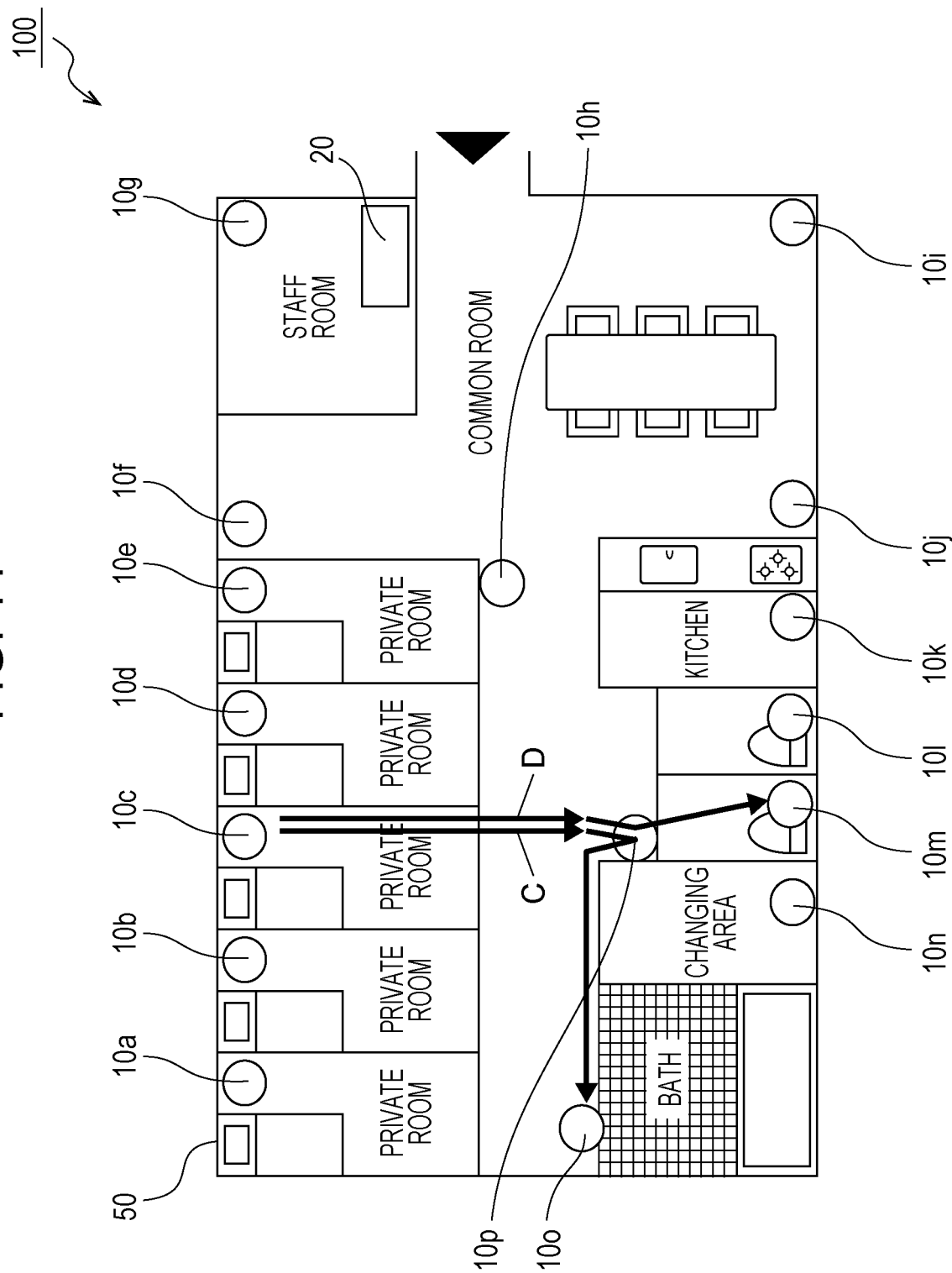
FIG. 14 is a diagram for explaining propagation paths.

For example, the correspondence relationships expressed by the table information illustrated in FIG. 13A above anticipate that the pathogen will propagate in order from the pathogen detector 10c, to the pathogen detector 10p, and then to the pathogen detector 10m. In other words, a propagation path D in FIG. 14 is anticipated. FIG. 14 is a diagram for explaining propagation paths.

Here, FIG. 15 is a table illustrating another example of the detection results stored in the second storage unit 22. In accordance with detection results as illustrated in FIG. 15, if the pathogen is assumed to propagate through the pathogen detectors in order of highest pathogen concentration, the pathogen conceivably propagates in order from the pathogen detector 10c, to the pathogen detector 10p, and then to the pathogen detector 10o. In other words, in FIG. 14, the pathogen conceivably propagates along the propagation path C rather than the propagation path D.

Figure 16:
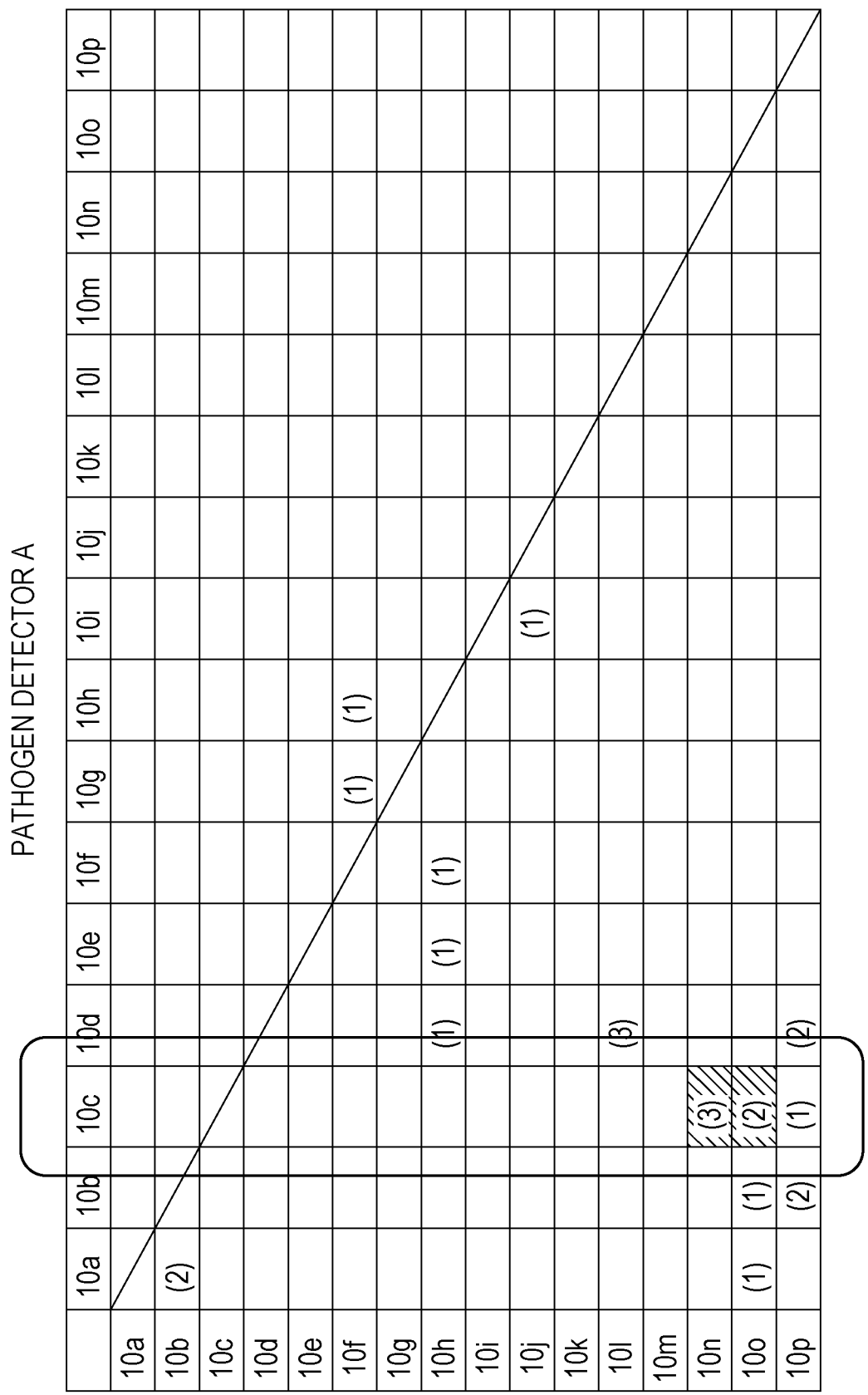
FIG. 16 is a diagram illustrating an example of updated table information.

In such a case, the second control unit 23 updates the correspondence relationships expressed by the table information illustrated in FIG. 13A in accordance with the pathogen concentrations detected by the pathogen detectors 10a to 10p as illustrated in FIG. 16. FIG. 16 is a diagram illustrating an example of updated table information. Note that in FIG. 16, the notation of numerical values in the table is omitted for the cases where the pathogen detectors 10j to 10p are used as the pathogen detector A.

As indicated by the hatched portion in the updated table information illustrated in FIG. 16, in the column corresponding to the pathogen detector 10c, (2) is contained in the row corresponding to the pathogen detector 10o rather than the row corresponding to the pathogen detector 10m.

In this way, if the table information is updated in accordance with the pathogen concentrations detected by the pathogen detectors 10a to 10p, control is possible in which the detection time interval is shortened more for pathogen detectors where the measured value of the pathogen concentration is higher and there is great need to detect the pathogen concentration, for example. Control is also possible in which the time interval of pathogen concentration detection is lengthened more for pathogen detectors where the measured value of the pathogen concentration is lower and there is little need to detect the pathogen concentration. Consequently, the pathogen detection system 100 is capable of efficiently detecting the pathogen concentration in the air inside the nursing home 50.

Embodiment 2

[Configuration and Operation]

Figure 17:
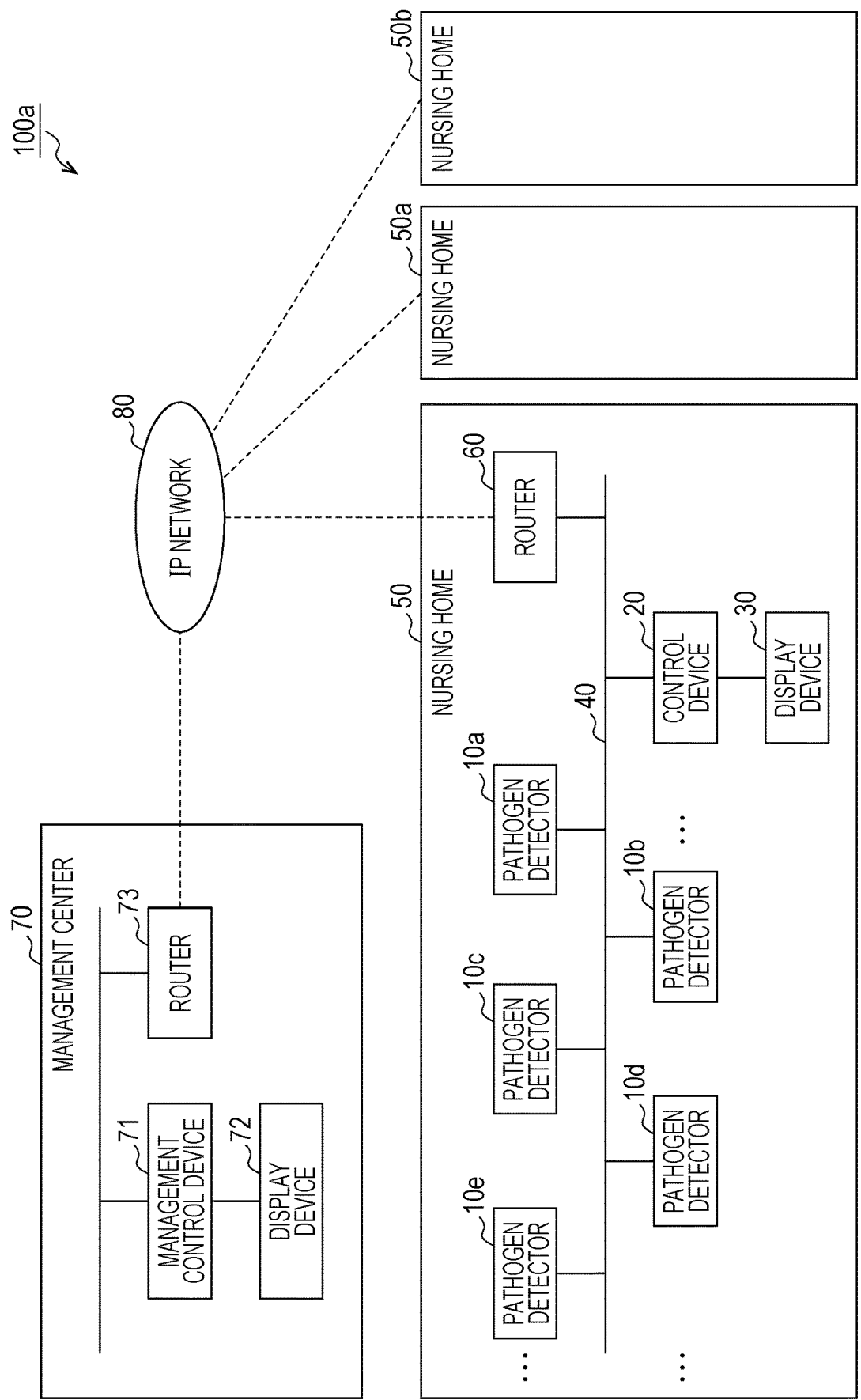
FIG. 17 is a block diagram illustrating an overall configuration of a pathogen detection system according to Embodiment 2.

In Embodiment 1 above, the control device 20 provided in the nursing home 50 transmits the command for changing the operating mode in accordance with the detection results from the pathogen detectors 10a to 10p. Alternatively, a control device installed outside the nursing home 50 may transmit the command for changing the operating mode in accordance with the detection results from the pathogen detectors 10a to 10p. FIG. 17 is a block diagram illustrating an overall configuration of the pathogen detection system according to Embodiment 2.

As illustrated in FIG. 17, a pathogen detection system 100a according to Embodiment 2 includes pathogen detectors 10a to 10p provided in a nursing home 50, a control device 20, and a display device 30, and furthermore includes a management control device 71, a display device 72, and a router 73 provided in a management center 70 positioned outside the nursing home 50. Additionally, the pathogen detection system 100a includes a router 60 provided in the nursing home 50.

Each of the router 60 provided in the nursing home 50 and the router 73 provided in the management center 70 is connected to an IP network 80. With this arrangement, the management control device 71 provided in the management center 70 is capable of communicating with the pathogen detectors 10a to 10p provided in the nursing home 50.

The management control device 71 is a server, for example, and has a functional configuration similar to the control device 20. In other words, the management control device 71 receives detection results from the pathogen detectors 10a to 10p provided in the nursing home 50, each detection result including the pathogen concentration detected by the corresponding pathogen detector, and stores the received detection results from the pathogen detectors 10a to 10p in a storage unit. Also, in the case where the pathogen concentration detected by one of the pathogen detectors 10a to 10p satisfies a predetermined condition, the management control device 71 issues a command for changing the operating mode for detecting the pathogen concentration from the first mode to the second mode to one or more other pathogen detectors among the pathogen detectors 10a to 10p.

FIG. 17 also illustrates a nursing home 50a and a nursing home 50b in addition to the nursing home 50. Although not illustrated, each of the nursing home 50a and the nursing home 50b includes pathogen detectors, a control device, and a display device like the nursing home 50. With this arrangement, the management control device 71 is also capable of issuing commands for changing the operating mode to the pathogen detectors provided in the nursing home 50a or the pathogen detectors provided in the nursing home 50b.

In addition, the management control device 71 may also issue the command for changing the operating mode in units of nursing homes. For example, in the case where the pathogen concentration detected by a pathogen detector provided in the nursing home 50 satisfies a predetermined condition, the management control device 71 may issue a command for changing the operating mode of the pathogen detectors provided in one or more other nursing homes near the nursing home 50 from among nursing homes. In this way, in accordance with the pathogen concentration detected in one nursing home, the pathogen detection system 100a is capable of changing the operating mode of the pathogen detectors inside another or other nursing homes belonging to a geographical area relatively near the one nursing home.

Modification of Operations in Embodiment 2

Figure 18:
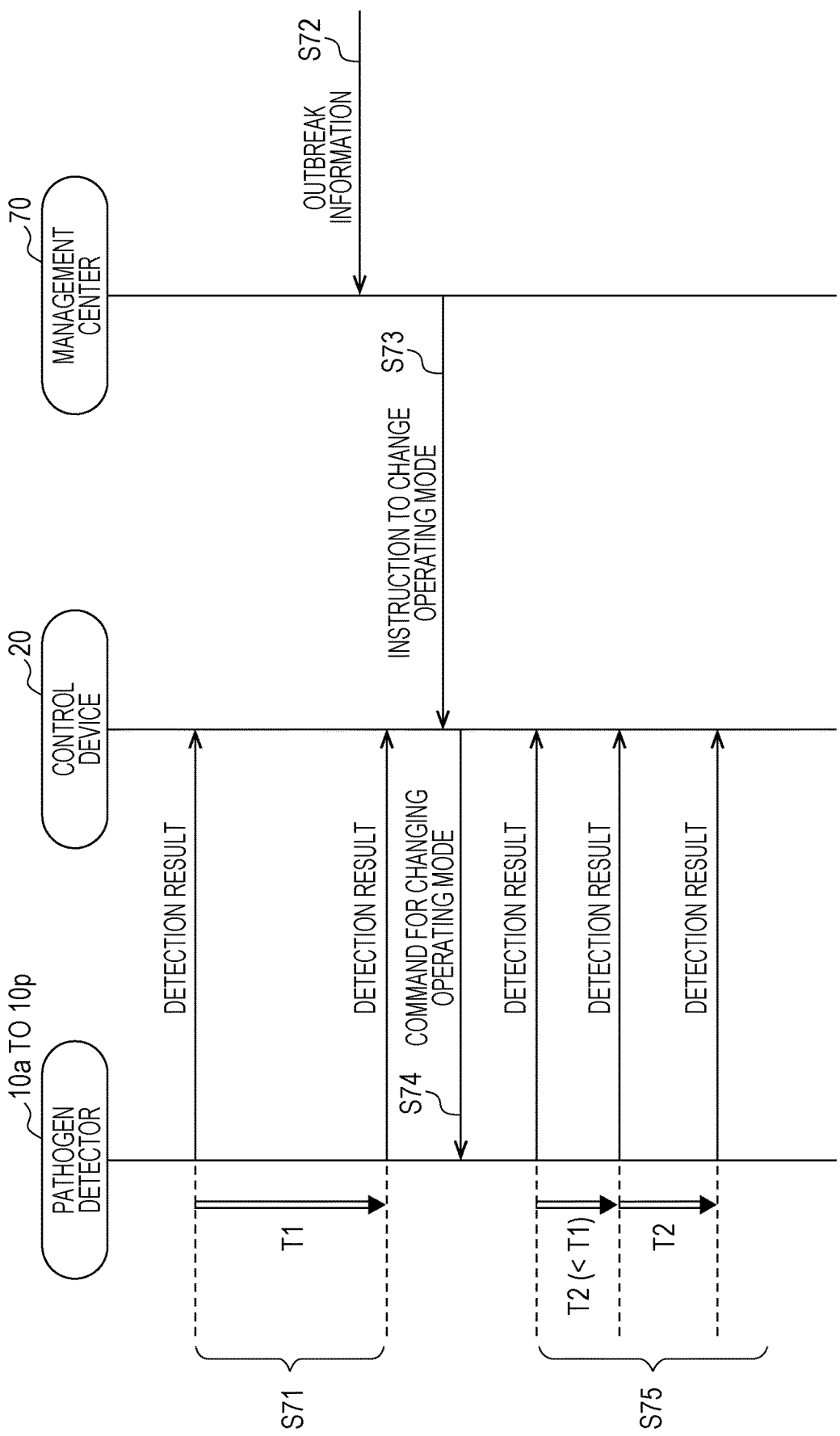
FIG. 18 is a communication sequence diagram illustrating a modification of operations by the pathogen detection system according to Embodiment 2.

In the pathogen detection system 100a, the control device 20 provided in the nursing home 50 may change the operating mode of the pathogen detectors 10a to 10p provided in the nursing home 50 in accordance with an instruction from the management control device 71. FIG. 18 is a communication sequence diagram illustrating a modification of such operations by the pathogen detection system 100a.

As illustrated in FIG. 18, the pathogen detectors 10a to 10p provided in the nursing home 50 are initially operating in the first mode. Each of the pathogen detectors 10a to 10p detects the pathogen concentration at the first time intervals T1, and transmits a detection result to the control device 20 every time a detection is performed (S71).

On the other hand, when outbreak information delivered from an external device is received (S72), the management control device 71 transmits an instruction to change the operating mode to the control device 20 (S73). Outbreak information is information for notifying facilities that an epidemic of an infectious disease caused by a pathogen has occurred. The delivery of outbreak information and the transmission of the instruction to change the operating mode in accordance with the delivered outbreak information mean that there is great need to detect the pathogen concentration.

Accordingly, if the instruction to change the operating mode is received, the control device 20 transmits the command for changing the operating mode to the pathogen detectors 10a to 10p (S74). When each of the pathogen detectors 10a to 10p receives the command for changing the operating mode, the pathogen detector changes the operating mode from the first mode to the second mode. Each of the pathogen detectors 10a to 10p operating in the second mode detects the pathogen concentration at the second time intervals T2 each of which is shorter than each of the first time intervals T1 (S75).

In this way, when there is great need to detect the pathogen concentration in accordance with outbreak information, the pathogen detection system 100a shortens the time interval of pathogen concentration detection by the pathogen detectors. In other words, when there is little need to detect the pathogen concentration, the time interval of pathogen concentration detection by the pathogen detectors is lengthened. Consequently, the pathogen detection system 100a is capable of efficiently detecting the pathogen concentration in the air inside the nursing home 50.

Other Embodiments

The foregoing describes embodiments of the present disclosure, but the present disclosure is not limited to the above embodiments.

For example, the above embodiments describe a case of detecting the pathogen concentration as the way of detecting the pathogen, but the pathogen detection may be a detection of an absolute quantity of the pathogen, or a detection of the existence of the pathogen. The absolute quantity of the pathogen can be detected by using an image sensor to acquire an image of the pathogen bonded to luminescent particles, and counting the number of light emission points in the acquired image, for example. Also, the existence of the pathogen can be detected according to the presence or absence of color development using commonly known immunochromatography.

In the foregoing embodiments, for example, the first mode and the second mode are modes having different time intervals for performing the pathogen concentration detection, but it is sufficient for the first mode and the second mode to exhibit different performance in the detection of the pathogen concentration. For example, the first mode and the second mode may be modes having different collection times for collecting the pathogen in a single detection. In this case, for example, when the pathogen concentration is relatively high, the collection time can be shortened to detect the pathogen efficiently.

Also, the detection-related modes are not limited to the two modes of the first mode and the second mode, and may also include a third mode that is different from the first and second modes.

Also, in the foregoing embodiments, a condition related to the pathogen concentration is used as the predetermined condition, but another condition may be used. For example, the predetermined condition may be a condition related to the absolute quantity of the pathogen, or a condition related to the existence of the pathogen, or in other words, the presence or absence of the pathogen.

For example, the foregoing embodiments describe an example in which the pathogen detection system is used in a nursing home, but the pathogen detection system may be used in a building such as a hospital, a school, or an airport, and may also be used outside.

Further, in the foregoing embodiments, the control device is described as a separate device from the pathogen detectors. However, one of the pathogen detectors may have the functions of the control device by including the control device built in the pathogen detector. Also, each of the pathogen detectors may receive direct detection results from the other pathogen detectors without going through the control device, and a controller provided in each pathogen detector may change the operating mode in accordance with the received detection results.

Furthermore, the method of communication between devices described in the foregoing embodiments is an example. The method of communication between devices is not particularly limited. For example, the communication between devices may be wireless communication using a communication standard such as specified low-power radio, ZigBee (registered trademark), Bluetooth (registered trademark), or Wi-Fi (registered trademark). Also, instead of wireless communication, the communication between devices may be wired communication such as power line communication (PLC) or wired LAN.

In the foregoing embodiments, a process executed by a specific processing unit may be executed by a different processing unit. Also, the order of processes in the operations by the pathogen detection system described in the foregoing embodiments is an example. The order of processes may be changed, and processes may be executed in parallel.

Also, in the foregoing embodiments, structural elements such as the controller may also be realized by executing a software program appropriate for the structural element. Each structural element may be realized as a result of a program execution unit such as a CPU or a processor reading out and executing a software program recorded on a recording medium such as a hard disk or semiconductor memory.

Structural elements such as the controller may be realized by hardware. Structural elements such as the controller may be realized by a circuit or an integrated circuit. These circuits may constitute a single circuit as a whole, or may be respectively different circuits. Also, each of these circuits may be a general-purpose circuit or a special-purpose circuit.

Otherwise, embodiments may be obtained by making various modifications that would naturally occur to persons skilled in the art to the foregoing embodiments, and embodiments may be achieved by appropriately combining the structural elements and functions in the foregoing embodiments without departing from the gist of the present disclosure, and such embodiments are also included in the present disclosure.

The pathogen detection system according to the present disclosure is capable of detecting a pathogen such as the influenza virus suspended in indoor air. The pathogen detection system according to the present disclosure is particularly applicable to facilities such as hospitals and nursing homes for the elderly.

What is claimed is:

1. A pathogen detection system comprising:
pathogen detectors disposed in different locations; and
a memory configured to store a program; and
a processor configured to execute the program and control the pathogen detection system to perform as follows, wherein
the pathogen detectors include a first pathogen detector performing a first pathogen detection, a second pathogen detector performing a second pathogen detection, and a third pathogen detector performing a third pathogen detection,
the first pathogen detector is configured to transmit a first detection result obtained as a result of the first pathogen detection to the processor,
the second pathogen detector is configured to transmit a second detection result obtained as a result of the second pathogen detection to the processor, and
in a case where the first detection result satisfies a predetermined condition, the processor is configured to cause the second pathogen detector to change a mode related to the second pathogen detection from a first mode to a second mode and not to cause the third pathogen detector to change a mode related to the third pathogen detection, thereby time intervals at which the third pathogen detector performing the third pathogen detection being unchanged before and after the processor causes the second pathogen detector to change the mode,
the predetermined condition is that a pathogen concentration obtained as the first detection result is lower than a predetermined reference concentration,
in the first mode, the processor is configured to cause the second pathogen detector to perform the second pathogen detection at fixed time intervals,
in the second mode, the processor is configured to cause the second pathogen detector to stop the second pathogen detection, and
the memory stores information indicating that a pathogen transmission distance between the first pathogen detector and the second pathogen detector is shortest among pathogen transmission distances between a plurality of pathogen detectors, each of the pathogen transmission distances being a distance between the first pathogen detector and each of the pathogen detectors other than the first pathogen detector, a pathogen transmission distance between the first pathogen detector and the third pathogen detector is second shortest among the pathogen transmission distances.

2. The pathogen detection system according to claim 1, wherein
the pathogen transmission distances are determined in accordance with information about a layout of a building and information about the locations where the pathogen detectors are respectively installed.

3. The pathogen detection system according to claim 1, wherein
the pathogen transmission distances are updated in accordance with pathogen concentration detection results detected by the pathogen detectors.

4. The pathogen detection system according to claim 1, further comprising:
a display that displays information based on pathogen concentrations detected by the pathogen detectors.

5. A pathogen detection system comprising:
pathogen detectors disposed in different locations; and
a memory configured to store a program; and
a processor configured to execute the program and control the pathogen detection system to perform as follows, wherein
the pathogen detectors include a first pathogen detector performing a first pathogen detection, a second pathogen detector performing a second pathogen detection, and a third pathogen detector performing a third pathogen detection,
the first pathogen detector is configured to transmit a first detection result obtained as a result of the first pathogen detection to the processor,
the second pathogen detector is configured to transmit a second detection result obtained as a result of the second pathogen detection to the processor,
in a case where the first detection result satisfies a predetermined condition, the processor is configured to cause the second pathogen detector to change a mode related to the second pathogen detection from a first mode to a second mode and not to cause the third pathogen detector to change a mode related to the third pathogen detection, thereby time intervals at which the third pathogen detector performing the third pathogen detection being unchanged before and after the processor causes the second pathogen detector to change the mode, the predetermined condition is that a pathogen concentration obtained as the first detection result is lower than a predetermined reference concentration, in the first mode, the processor is configured to cause the second pathogen detector to detect a second pathogen concentration at second time intervals, in the second mode, the processor is configured to cause the second pathogen detector to detect a third pathogen concentration at first time intervals, each of the second time intervals being shorter than each of the first time intervals, and the memory stores information indicating that a pathogen transmission distance between the first pathogen detector and the second pathogen detector is shortest among pathogen transmission distances between a plurality of pathogen detectors, each of the pathogen transmission distances being a distance between the first pathogen detector and each of the pathogen detectors other than the first pathogen detector, a pathogen transmission distance between the first pathogen detector and the third pathogen detector being second shortest among the pathogen transmission distances.

6. The pathogen detection system according to claim 5, wherein the pathogen transmission distances are determined in accordance with information about a layout of a building and information about the locations where the pathogen detectors are respectively installed.

7. The pathogen detection system according to claim 5, wherein the pathogen transmission distances are updated in accordance with pathogen concentration detection results detected by the pathogen detectors.

8. The pathogen detection system according to claim 5, further comprising:

a display that displays information based on pathogen concentrations detected by the pathogen detectors.

* * * * *